US011291858B2

(12) United States Patent
MacDonald et al.

(10) Patent No.: US 11,291,858 B2
(45) Date of Patent: Apr. 5, 2022

(54) RADIATION TREATMENT PLANNING WITH MULTIPLE TARGET SUBSET OPTIMIZATION

(71) Applicant: DALHOUSIE UNIVERSITY, Halifax (CA)

(72) Inventors: Robert Lee MacDonald, Antigonish (CA); Alasdair Syme, Halifax (CA); Christopher G. Thomas, Halifax (CA)

(73) Assignee: Dalhousie University, Haiifax (CA)

( * ) Notice: Subject to any disclaimer, the term of this patent is extended or adjusted under 35 U.S.C. 154(b) by 148 days.

(21) Appl. No.: 16/870,665

(22) Filed: May 8, 2020

(65) Prior Publication Data
US 2020/0346033 A1 Nov. 5, 2020

Related U.S. Application Data

(63) Continuation of application No. PCT/CA2018/051418, filed on Nov. 8, 2018.

(60) Provisional application No. 62/583,412, filed on Nov. 8, 2017.

(51) Int. Cl.
A61N 5/10 (2006.01)
(52) U.S. Cl.
CPC ......... A61N 5/1031 (2013.01); A61N 5/1045 (2013.01); A61N 5/1077 (2013.01)
(58) Field of Classification Search
None
See application file for complete search history.

(56) References Cited

U.S. PATENT DOCUMENTS

| 7,496,173 | B2 | 2/2009 | Goldman et al. |
| 8,913,717 | B2* | 12/2014 | Siljamaki ............. A61N 5/1031 378/65 |
| 9,061,142 | B2* | 6/2015 | Vilsmeier ................ G21K 5/04 |
| 9,507,886 | B2 | 11/2016 | Fiege et al. |
| 2013/0142310 | A1 | 6/2013 | Fahimian et al. |
| 2019/0247676 | A1* | 8/2019 | Peltola ................. A61N 5/1077 |
| 2021/0101021 | A1* | 4/2021 | Fredriksson ......... A61N 5/1031 |

(Continued)

FOREIGN PATENT DOCUMENTS

| WO | 2013075743 A1 | 5/2013 |
| WO | 2015039903 A1 | 3/2015 |
| WO | 2016/008052 A1 | 1/2016 |

(Continued)

OTHER PUBLICATIONS

Kang et al., "A method for optimizing LINAC treatment geometry for volumetric modulated arc therapy of multiple brain metastases", Medical Physics, vol. 37, No. 8, Aug. 2010, pp. 4146-4154.

Primary Examiner — Hoon K Song
(74) Attorney, Agent, or Firm — Oyen Wiggs Green & Mutala LLP

(57) ABSTRACT

Generating a plan for radiation treatment of multiple target volumes such as, for example, multiple brain tumors, involves optimizing a grouping of the target volumes into subsets and generating treatment plans for each subset. Resulting treatment plans may minimize radiation dose to tissues outside of the target volumes. A radiation treatment planning system may be configured to operate in this manner and to upload control signals which cause a radiation therapy device such as a linear accelerator to execute the radiation treatment plans.

20 Claims, 14 Drawing Sheets

(56) References Cited

U.S. PATENT DOCUMENTS

2021/0244970 A1* 8/2021 MacDonald ........... A61N 5/103

FOREIGN PATENT DOCUMENTS

| WO | 2016/009271 A1 | 1/2016 |
| WO | 2017/152286 A1 | 9/2017 |

* cited by examiner

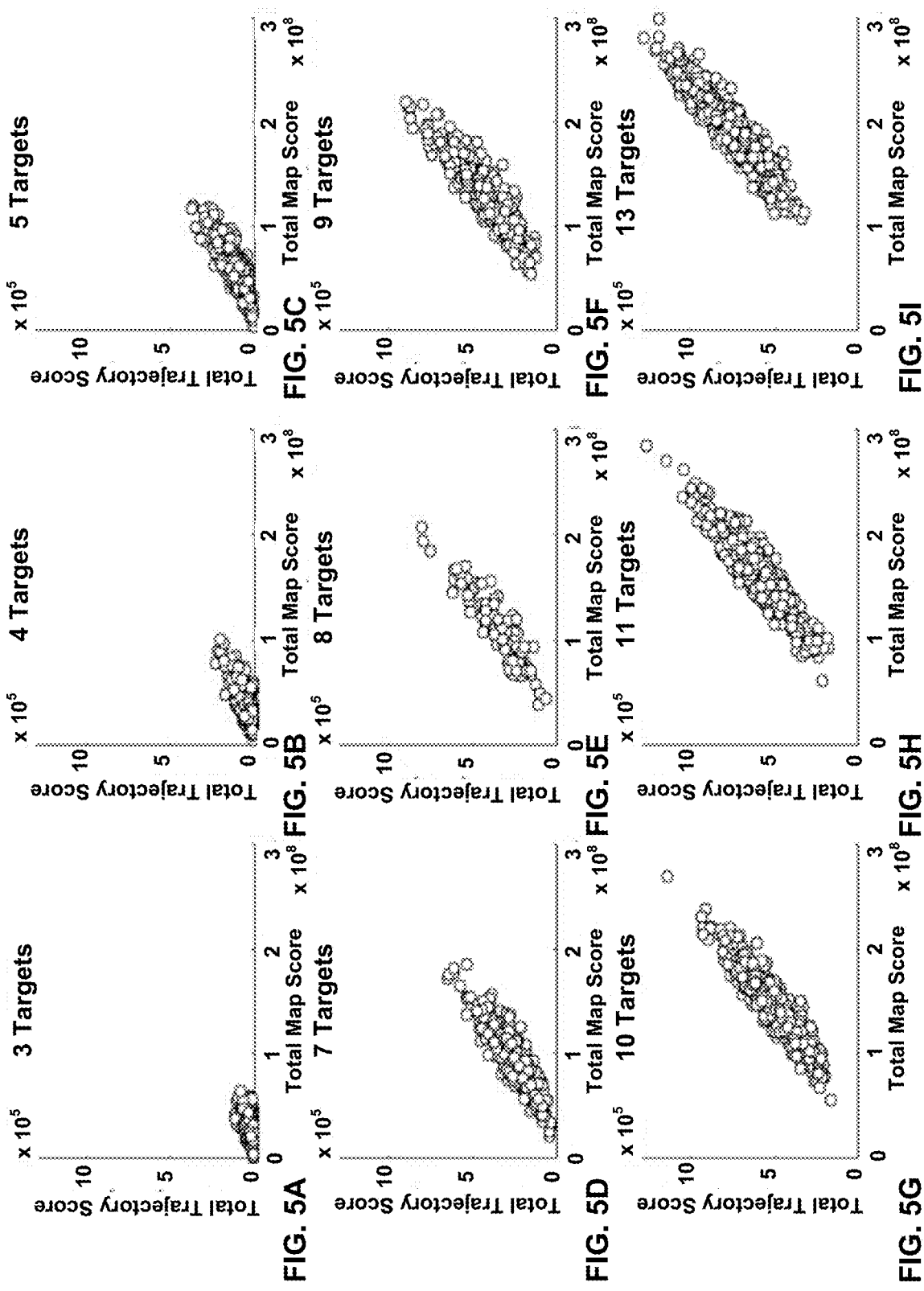

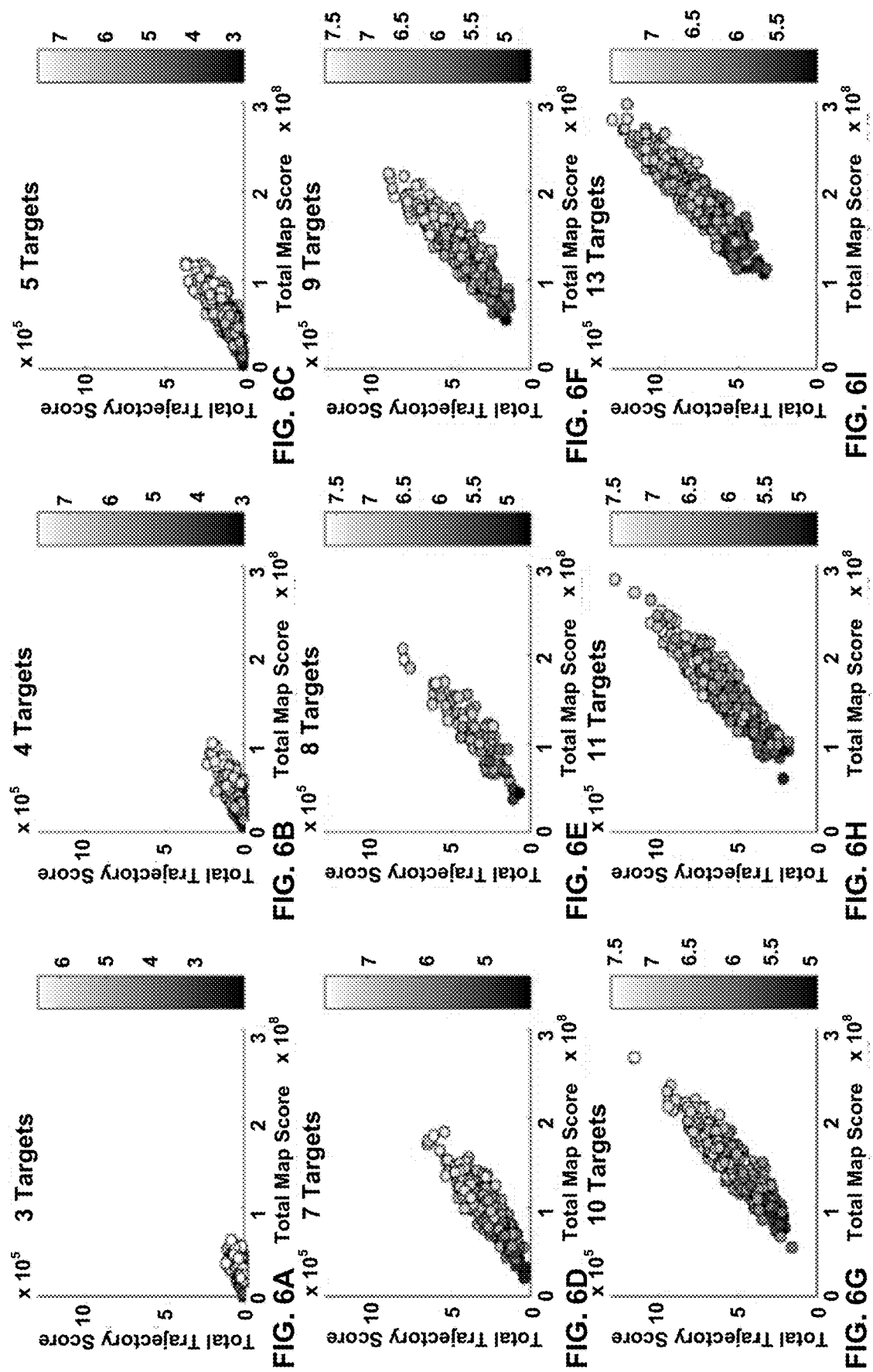

— 1 —

RADIATION TREATMENT PLANNING WITH MULTIPLE TARGET SUBSET OPTIMIZATION

CROSS-REFERENCE TO RELATED APPLICATION

This application is a continuation of PCT Application No. PCT/CA 2018/051418 filed 8 Nov. 2018, which claims priority from U.S. Application No. 62/583,412 filed 8 Nov. 2017. For purposes of the United States, this application claims the benefit under 35 U.S.C. § 119 of U.S. Application No. 62/583,412 filed 8 Nov. 2017 and entitled RADIATION TREATMENT PLANNING WITH MULTIPLE TARGET SUBSET OPTIMIZATION which is hereby incorporated herein by reference for all purposes.

FIELD

The present disclosure relates to radiotherapy systems and methods. Some embodiments provide systems and methods useful in planning and/or delivering radiotherapy by arc therapy.

BACKGROUND

Radiotherapy involves delivering radiation to a subject. A non-limiting example application of radiotherapy is cancer treatment. Radiotherapy is widely used for treating tumors in the brain, for example. The radiation used for radiotherapy may comprise photon beams (e.g. x-rays) or particle beams (e.g. proton beams). Radiation for treatment of cancers and other conditions may, for example, be generated by a linear accelerator.

Ideally a radiotherapy treatment could deliver a prescribed radiation dose to a target volume (e.g. a brain tumor) while delivering no radiation outside of the target volume. This is not possible, in general, because the radiation beams used for radiotherapy must typically pass through overlying tissues to reach a target volume. The radiation beams deliver radiation dose to these overlying tissues as they pass through them. Further, the radiation beams are not extinguished in the target volume. The radiation beams pass through the target volume and deliver dose to tissues on the side of the target volume away from the radiation source. Scattering of radiation from a radiation beam is another mechanism by which radiation dose is delivered outside of a target volume.

Although it is impossible to avoid delivering radiation dose to tissues outside of a target volume, the amount of dose delivered outside of the target volume and the way in which that dose is distributed in non-target tissues can be affected very significantly by how the radiation is delivered to the target volume. For example, a target volume may be irradiated by radiation beams incident from many directions which collectively deliver a prescribed dose to the target volume. This may result in relatively low doses to individual volumes of tissue outside of the target volume while achieving a distribution of dose within the target volume that more accurately matches a prescription (for example, the prescription may call for a specified uniform dose within the target volume).

The field of radiation treatment planning has been and remains the subject of a large amount of active research. This research has yielded various approaches to planning and delivering radiotherapy.

Arc therapies are a class of radiotherapy which involve moving a radiation source along a treatment trajectory (typically an arc) extending at least part way around a patient. Radiation doses are delivered to a target volume from locations on the trajectory. In some arc therapies, radiation is delivered continuously or substantially continuously as the radiation source is moved along the trajectory. By irradiating target volumes from a variety of angles, arc therapies aim to achieve the prescription doses assigned to planning target volumes while limiting the radiation exposure to healthy normal tissue and any sensitive structures.

Conformal arc therapies involve shaping a radiation beam (for example a cone beam), such that a cross-section of the beam is shaped to conform with the projection of the target volume in the beam's-eye-view (i.e. a view taken along a central axis of the radiation beam, abbreviated as BEV). Beam shaping is typically achieved by passing the beam through a beam shaper having an aperture that can be adjusted to conform at least roughly to the shape of the projection of the target volume. Deviations between the shape of the aperture and the boundary of the projection of the target volume are another source of dose to non-target tissues and/or deviations from prescribed dose within the target volume.

One type of beam shaper is a multiple leaf collimator (MLC). A MLC has two sets of leaves that can be advanced or retracted from either side of an opening to define a desired aperture. In some treatment modalities, positions of the leaves of a MLC are adjusted dynamically to change the shaping of a radiation beam as the beam source is moved along a trajectory. MLCs are available commercially from companies including Varian, Siemens and Elekta.

For target volumes having certain shapes, the degree to which a radiation beam can be shaped by the leaves of a MLC to match the shape of the projection of the target volume can depend on the relative orientations of the target volume and the MLC leaves. Some arc therapy modalities that apply a MLC allow the MLC to be rotated to optimize beam shaping to match the projection of a target volume for different points along the trajectory. Arc therapies include, but are not limited to, dynamic conformal arcs and volumetric modulated arc therapy.

One type of arc therapy is intensity modulated arc therapy (IMAT). IMAT involves modulating the intensity of a radiation field. The intensity modulated radiation field can be shaped (for example, using a MLC) to improve conformation of a delivered dose distribution to a prescribed dose distribution.

In general, beam shapers, including MLCs, cannot completely block parts of a radiation beam. Radiation that leaks through the beam shaper outside of the aperture (e.g. through MLC leaves or through the joints between MLC leaves) can deliver non-negligible doses to non-targeted tissues.

Some non-target tissues may be more sensitive to radiation exposure and/or critical than others. Such non-target tissue may be called an organ-at-risk (OAR). It can be desirable to minimize dose delivered to OARs. For example, in delivering radiation to locations within a patient's brain, it is generally desirable to minimize dose delivered to the patient's optic nerves and brainstem, each of which may be considered to be an OAR in at least some applications.

In treatment of some medical conditions it can be desirable to treat plural targets. For example, a brain cancer may spread to a number of sites in a patient's brain. Radiotherapy to treat such brain cancers may involve delivering radiation doses to multiple target volumes.

A problem with planning radiation treatment for the case where there are multiple target volumes is that for at least some angles it may not be possible to configure a beam shaper such as a MLC to form a beam that simultaneously covers all target volumes while the MLC blocks delivery of radiation to tissues outside of the target volumes.

There is a need for improved systems, methods and apparatus for planning and/or delivering radiation treatments.

SUMMARY

This invention has a number of aspects. These include, without limitation:
 radiation treatment planning apparatus and methods;
 apparatus and methods for controlling radiotherapy apparatus such as medical linear accelerator systems; and
 apparatus and methods for delivering radiation treatments.

The invention has particular application to planning radiation treatment and/or delivery of radiation treatment in cases where there are multiple target volumes.

One aspect of the invention provides a method for generating a radiation treatment plan for delivery of radiation to a set comprising a plurality of target volumes using a radiation treatment system comprising a beam shaper, each of the target volumes associated with a prescribed radiation dose. The method comprises dividing the set of target volumes into two or more optimized subsets of the set of target volumes by a process comprising: computing a metric for each of a plurality of subsets of the set of target volumes, the metric correlated to how well the beam shaper can conform a radiation beam to the target volumes corresponding to each of the plurality of subsets; and selecting as the two or more optimized subsets those of the plurality of subsets which contain all of the plurality of target volumes without overlap for which an overall metric obtained by mathematical combination of the metrics for the plurality of subsets is an extremum. The method also comprises determining a treatment plan for each of the two or more optimized subsets, the treatment plans specifying configurations for the beam shaper for control points along a radiation source trajectory, each configuration selected to shape the radiation beam to deliver radiation to the target volumes of the respective subset. Any known or future-developed method may be applied for determining the treatment plans for the optimized subsets.

In some embodiments the method comprises providing each of the treatment plans in the form of control signals that may be applied to control the radiation treatment system to deliver radiation using the corresponding trajectory and configurations for the beam shaper.

In some embodiments computing the metric for each of the plurality of subsets determines lengths of axes of a three-dimensional bounding volume enclosing centers of mass of the target volumes of the respective subset and computing a function of the lengths of the axes.

In some embodiments the bounding volume encloses the target volumes of the respective subset.

In some embodiments the bounding volume is an ellipsoid or a rectangular prism.

In some embodiments an orientation of the bounding volume is fixed.

In some embodiments an orientation of one or more of the axes of the bounding volume is adjustable by at least one of user input and in response to analysis of a spatial distribution of the target volumes.

In some embodiments the method comprises setting the orientation of one or more of the axes of the bounding volume in response to analysis of the spatial distribution of the target volumes by orienting one or more of the axes of the bounding volume to align with one or more principal axes of the spatial distribution of the target volumes.

In some embodiments determining the treatment plan for each of the two or more optimized subsets selects different trajectories for delivering radiation to at least two of the optimized subsets.

In some embodiments the function is also a function of the volumes of the target volumes of the respective subset.

In some embodiments the function combines a representative value for magnitudes of the target volumes of a subset by a representative value for dimensions of a bounding volume for the subset.

In some embodiments the method comprises seeking an optimal grouping of subsets that provides an extremum of the overall metric by applying a simulated annealing algorithm.

In some embodiments the simulated annealing algorithm comprises a plurality of iterations, each of the plurality of iterations comprising generating a new group of subsets and determining a value of the overall metric for the new group of subsets.

In some embodiments generating the new group of subsets comprises interchanging two of the target volumes that are in different subsets of a current group of subsets.

In some embodiments generating the new group of subsets comprises moving a target volume from a first subset to a second subset.

In some embodiments generating the new group of subsets is random.

In some embodiments generating the new group of subsets is quasi-random.

In some embodiments the simulated annealing algorithm comprises generating a starting group by randomly assigning each target volume of the set of target volumes to one of a plurality of subsets.

In some embodiments the simulated annealing algorithm comprises generating a starting grouping of subsets by assigning each target volume of the set of target volumes to one of a plurality of subsets in an order.

In some embodiments the method comprises determining a value of the overall metric for the starting group of subsets.

In some embodiments the method comprises comparing the value of the overall metric for the new group of subsets to the value of the overall metric for the starting group of subsets to find a group that is better than the starting group.

In some embodiments dividing the set of target volumes into the two or more optimized subsets comprises identifying all possible subsets of the set of target volumes and computing the metric for each of the possible subsets.

In some embodiments the method comprises constraining the possible subsets by requiring a number of the target volumes to be included in each of the subsets to be within a set range.

In some embodiments a lower end of the range is three target volumes in each subset.

In some embodiments the method comprises constraining the possible subsets by requiring that all of the plurality of target volumes be contained in no more than a set number of non-overlapping subsets.

In some embodiments the set number is in a range of 2 to 5.

In some embodiments selecting the two or more optimized subsets comprises randomly generating a number of groupings of subsets of the set of target volumes wherein each of the groupings contains all of the plurality of target volumes without overlap, determining the overall metric for each grouping and selecting as the two or more optimized subsets those subsets belonging to the one of the groupings for which the value of the overall metric correlates to a minimized amount of whitespace.

In some embodiments determining the radiation treatment plan for one of the optimized subsets comprises taking into account calculated radiation dose that would be delivered to the target volumes of the respective subset by executing a radiation treatment plan for one or more other ones of the optimized subsets.

In some embodiments determining the treatment plan comprises calculating a cumulative dose map that would result from delivery of each of the radiation treatment plans for all of the optimized subsets.

In some embodiments determining the radiation treatment plan comprises selecting configurations of the beam shaper that minimize an amount of whitespace of the trajectory.

In some embodiments selecting configurations of the beam shaper that minimize the amount of whitespace of the trajectory comprises performing a bi-direction gradient algorithm.

In some embodiments the configurations of the beam shaper comprise rotation angles of the beam shaper along the radiation source trajectory.

In some embodiments the beam shaper comprises a multileaf collimator and specifying configurations for the beam shaper comprises specifying leaf positions for the multileaf collimator for each of the control points.

In some embodiments the control points are spaced apart along an arc at angular intervals of 3 degrees or less.

In some embodiments the radiation delivery machine comprises a linear accelerator.

In some embodiments the metric for each of the plurality of subsets of the set of target volumes is computed according to an equation:

$$M = \log(\overline{V} * \overline{A})$$

wherein M is a value of the metric for the respective subset, $\overline{V}$ is a mean of all target volumes in the respective subset and $\overline{A}$ is a mean of lengths of axes of a three-dimensional bounding volume.

In some embodiments the metric for each of the plurality of subsets of the set of target volumes is computed according to an equation:

$$M = \frac{a * \sum V}{\sigma_V} + \frac{b * \sum S}{\sigma_S}$$

wherein M is a value of the metric for the respective subset, V is a volume of a target volume in the respective subset, a and b are weighting factors, $\sigma_v$ is a normalization factor, $\Sigma S$ is a sum of lengths of axes of a three-dimensional bounding volume and $\sigma_s$ is a normalization factor.

In some embodiments $\sigma_v$ is one of a value of a standard deviation of volumes V of target volumes in the set of target volumes, a standard deviation of volumes V of target volumes in the plurality of subsets, a standard deviation of volumes V of target volumes in the respective subset and a standard deviation of volumes V of target volumes in the two or more optimized subsets.

In some embodiments $\sigma_s$ is a value of a standard deviation of lengths of axes of three-dimensional bounding volumes in the plurality of subsets.

In some embodiments the overall metric for the plurality of subsets is computed according to an equation:

$$M_{OA} = M_1^2 + M_2^2 + \ldots + M_k^2$$

wherein $M_{OA}$ is a value of the overall metric for the plurality of subsets, $M_1$, $M_2$ and $M_k$ are computed metric values for each respective subset in the plurality of subsets and k is a value of a total number of subsets in the plurality of subsets.

In some embodiments the overall metric is computed according to an equation:

$$M_{OA} = \sqrt{M_1^2 + M_2^2 + \ldots + M_k^2}$$

wherein $M_{OA}$ is a value of the overall metric for the plurality of subsets, $M_1$, $M_2$ and $M_k$ are computed metric values for each respective subset in the plurality of subsets and k is a value of a total number of subsets in the plurality of subsets.

In some embodiments the overall metric is computed according to an equation:

$$M_{OA} = \Sigma_j M_j + \Sigma_{j \neq k}(M_j - M_k)$$

wherein $M_{OA}$ is a value of the overall metric for the plurality of subsets, $M_j$ is a computed metric value for a $j^{th}$ subset in the plurality of subsets and k is a value of a total number of subsets in the plurality of subsets.

In some embodiments the overall metric is computed according to an equation:

$$M_{OA} = \sqrt{\Sigma_j M_j^2} - \Sigma_{j \neq k}(M_j - M_k)$$

wherein $M_{OA}$ is a value of the overall metric for the plurality of subsets, $M_j$ is a computed metric value for a $j^{th}$ subset in the plurality of subsets and k is a value of a total number of subsets in the plurality of subsets.

One aspect of the invention provides a computer-readable physical memory having stored thereon computer-executable instructions which, when executed by a processor, cause the processor to perform any methods as described herein.

One aspect of the invention provides an apparatus for delivery of radiation to a set comprising a plurality of target volumes, each of the target volumes associated with a prescribed radiation dose. The apparatus comprises a radiation treatment system comprising a radiation source and a beam shaper. The apparatus also comprises a radiation treatment planning console in data communication with the radiation treatment system, the radiation treatment planning console comprising a processor connected to receive data specifying the set of target volumes to be treated by a radiation treatment plan. The processor is configured to divide the set of target volumes into two or more optimized subsets of the set of target volumes by a process comprising computing a metric for each of a plurality of subsets of the set of target volumes, the metric correlated to how well the beam shaper can conform a radiation beam to the target volumes corresponding to each of the plurality of subsets; and selecting as the two or more optimized subsets those of the plurality of subsets which contain all of the plurality of target volumes without overlap for which an overall metric obtained by mathematical combination of the metrics for the plurality of subsets is an extremum. The processor is also configured to determine a treatment plan for each of the two or more optimized subsets, the treatment plans specifying configurations for the beam shaper for control points along a radiation source trajectory, each configuration selected to shape the radiation beam to deliver radiation to the target volumes of the respective subset.

In some embodiments the processor is configured to provide each of the treatment plans in the form of control signals that may be applied to control the radiation treatment system to deliver radiation using the corresponding trajectory and configurations for the beam shaper.

In some embodiments the processor configured to compute the metric for each of the plurality of subsets comprises the processor configured to determine lengths of axes of a three-dimensional bounding volume enclosing centers of mass of the target volumes of the respective subset and computing a function of the lengths of the axes.

In some embodiments the bounding volume encloses the target volumes of the respective subset.

In some embodiments the bounding volume is an ellipsoid or a rectangular prism.

In some embodiments an orientation of the bounding volume is fixed.

In some embodiments the processor is configured to adjust an orientation of one or more of the axes of the bounding volume based on at least one of user input and in response to analysis of a spatial distribution of the target volumes.

In some embodiments the processor is configured to set the orientation of one or more of the axes of the bounding volume in response to analysis of the spatial distribution of the target volumes by orienting one or more of the axes of the bounding volume to align with one or more principal axes of the spatial distribution of the target volumes.

In some embodiments the processor configured to determine the treatment plan for each of the two or more optimized subsets comprises the processor configured to select different trajectories for delivering radiation to at least two of the optimized subsets.

In some embodiments the function is also a function of the volumes of the target volumes of the respective subset.

In some embodiments the function combines a representative value for magnitudes of the target volumes of a subset by a representative value for dimensions of a bounding volume for the subset.

In some embodiments the processor is configured to seek an optimal grouping of subsets that provides an extremum of the overall metric by applying a simulated annealing algorithm.

In some embodiments the processor configured to apply the simulated annealing algorithm comprises the processor configured to perform a plurality of iterations, each of the plurality of iterations comprising generating a new group of subsets and determining a value of the overall metric for the new group of subsets.

In some embodiments the processor configured to generate the new group of subsets comprises the processor configured to interchange two of the target volumes that are in different subsets of a current group of subsets.

In some embodiments the processor configured to generate the new group of subsets comprises the processor configured to move a target volume from a first subset to a second subset.

In some embodiments the processor is configured to generate the new group of subsets randomly.

In some embodiments the processor is configured to generate the new group of subsets quasi-randomly.

In some embodiments the processor configured to apply the simulated annealing algorithm comprises the processor configured to generate a starting group by randomly assigning each target volume of the set of target volumes to one of a plurality of subsets.

In some embodiments applying the simulated annealing algorithm comprises the processor configured to generate a starting grouping of subsets by assigning each target volume of the set of target volumes to one of a plurality of subsets in an order.

In some embodiments the processor is configured to determine a value of the overall metric for the starting group of subsets.

In some embodiments the processor is configured to compare the value of the overall metric for the new group of subsets to the value of the overall metric for the starting group of subsets to find a group that is better than the starting group.

In some embodiments the processor configured to divide the target volumes into the two or more optimized subsets comprises the processor configured to identify all possible subsets of the set of target volumes and compute the metric for each of the possible subsets.

In some embodiments the processor is configured to constrain the possible subsets by requiring a number of the target volumes to be included in each of the subsets to be within a set range.

In some embodiments a lower end of the range is three target volumes in each subset.

In some embodiments the processor is configured to constrain the possible subsets by requiring that all of the plurality of target volumes be contained in no more than a set number of non-overlapping subsets.

In some embodiments the set number is in a range of 2 to 5.

In some embodiments the processor configured to select the two or more optimized subsets comprises the processor configured to randomly generate a number of groupings of subsets of the set of target volumes wherein each of the groupings contains all of the plurality of target volumes without overlap, determine the overall metric for each grouping and select as the two or more optimized subsets those subsets belonging to the one of the groupings for which the value of the overall metric correlates to a minimized amount of whitespace.

In some embodiments the processor configured to determine the radiation treatment plan for one of the optimized subsets comprises the processor configured to take into account calculated radiation dose that would be delivered to the target volumes of the respective subset by executing a radiation treatment plan for one or more other ones of the optimized subsets.

In some embodiments the processor configured to determine the treatment plan comprises the processor configured to calculate a cumulative dose map that would result from delivery of each of the radiation treatment plans for all of the optimized subsets.

In some embodiments the processor configured to determine the radiation treatment plan comprises the processor configured to select configurations of the beam shaper that minimize an amount of whitespace of the trajectory.

In some embodiments the processor is configured to select configurations of the beam shaper that minimize the amount of whitespace of the trajectory by performing a bi-directional gradient algorithm.

In some embodiments the configurations of the beam shaper comprise rotation angles of the beam shaper along the radiation source trajectory.

In some embodiments the beam shaper comprises a multileaf collimator and the processor configured to specify configurations for the beam shaper comprises the processor configured to specify leaf positions for the multileaf collimator for each of the control points.

In some embodiments the control points are spaced apart along an arc at angular intervals of 3 degrees or less.

In some embodiments the radiation source comprises a linear accelerator.

In some embodiments the processor is configured to compute the metric for each of the plurality of subsets of the set of target volumes according to an equation:

$$M = \log(\overline{V} * \overline{A})$$

wherein M is a value of the metric for the respective subset, $\overline{V}$ is a mean of all target volumes in the respective subset and $\overline{A}$ is a mean of lengths of axes of a three-dimensional bounding volume.

In some embodiments the processor is configured to compute the metric for each of the plurality of subsets of the set of target volumes according to an equation:

$$M = \frac{a * \sum V}{\sigma_V} + \frac{b * \sum S}{\sigma_S}$$

wherein M is a value of the metric for the respective subset, V is a volume of a target volume in the respective subset, a and b are weighting factors, $\sigma_V$ is a normalization factor, $\Sigma S$ is a sum of lengths of axes of a three-dimensional bounding volume and $\sigma_s$ is a normalization factor.

In some embodiments $\sigma_V$ is one of a value of a standard deviation of volumes V of target volumes in the set of target volumes, a standard deviation of volumes V of target volumes in the plurality of subsets, a standard deviation of volumes V of target volumes in the respective subset and a standard deviation of volumes V of target volumes in the two or more optimized subsets.

In some embodiments $\sigma_s$ is a value of a standard deviation of lengths of axes of three-dimensional bounding volumes in the plurality of subsets.

In some embodiments the processor is configured to compute the overall metric for the plurality of subsets according to an equation:

$$M_{OA} = M_1^2 + M_2^2 + \ldots + M_k^2$$

wherein $M_{OA}$ is a value of the overall metric for the plurality of subsets, $M_1$, $M_2$ and $M_k$ are computed metric values for each respective subset in the plurality of subsets and k is a value of a total number of subsets in the plurality of subsets.

In some embodiments the processor is configured to compute the overall metric according to an equation:

$$M_{OA} = \sqrt{M_1^2 + M_2^2 + \ldots + M_k^2}$$

wherein $M_{OA}$ is a value of the overall metric for the plurality of subsets, $M_1$, $M_2$ and $M_k$ are computed metric values for each respective subset in the plurality of subsets and k is a value of a total number of subsets in the plurality of subsets.

In some embodiments the processor is configured to compute the overall metric according to an equation:

$$M_{OA} = \Sigma_j M_j + \Sigma_{j \neq k}(M_j - M_k)$$

wherein $M_{OA}$ is a value of the overall metric for the plurality of subsets, $M_j$ is a computed metric value for a $j^{th}$ subset in the plurality of subsets and k is a value of a total number of subsets in the plurality of subsets.

In some embodiments the processor is configured to compute the overall metric according to an equation:

$$M_{OA} = \sqrt{\Sigma_j N_j^2} - \Sigma_{i \neq k}(M_j - M_k)$$

wherein $M_{OA}$ is a value of the overall metric for the plurality of subsets, $M_j$ is a computed metric value for a $j^{th}$ subset in the plurality of subsets and k is a value of a total number of subsets in the plurality of subsets.

Some embodiments provide methods and systems for planning radiation treatments for cases in which there are a relatively large number of target volumes. For example, certain embodiments may be applicable to cases where there are at least 6, 9, 14, 17 or 20 target volumes.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

FIGS. 5A to 5I are scatter plots showing whitespace map scores for each of a number of targets.

FIGS. 6A to 6I show the data from FIGS. 5A to 5I in which each data point is replaced by a symbol which indicates the value of a metric corresponding to that data point.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
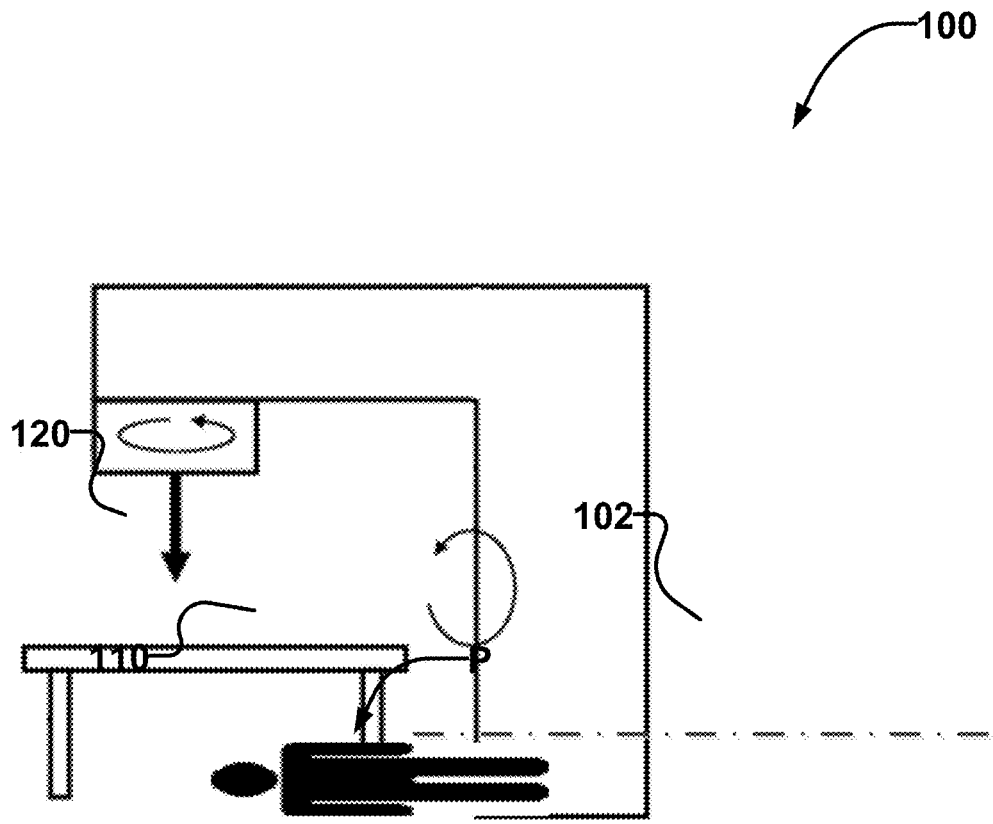
FIG. 1 is a schematic view of an example radiation delivery system.

FIG. 1 shows an example radiotherapy system 100 of a type that may be used for performing radiotherapy. The example system 100 includes a gantry 102, which houses a radiation source 120 (e.g. a linear accelerator) that can be controlled to emit a radiation beam 110 toward patient P. Gantry 102 may include motors to rotate the gantry, and thereby rotate the point of origin of radiation beam 110 in an arc around patient P. Radiotherapy systems that are generally similar to system 100 are commercially available from companies such as Varian and Elekta.

Figure 2:
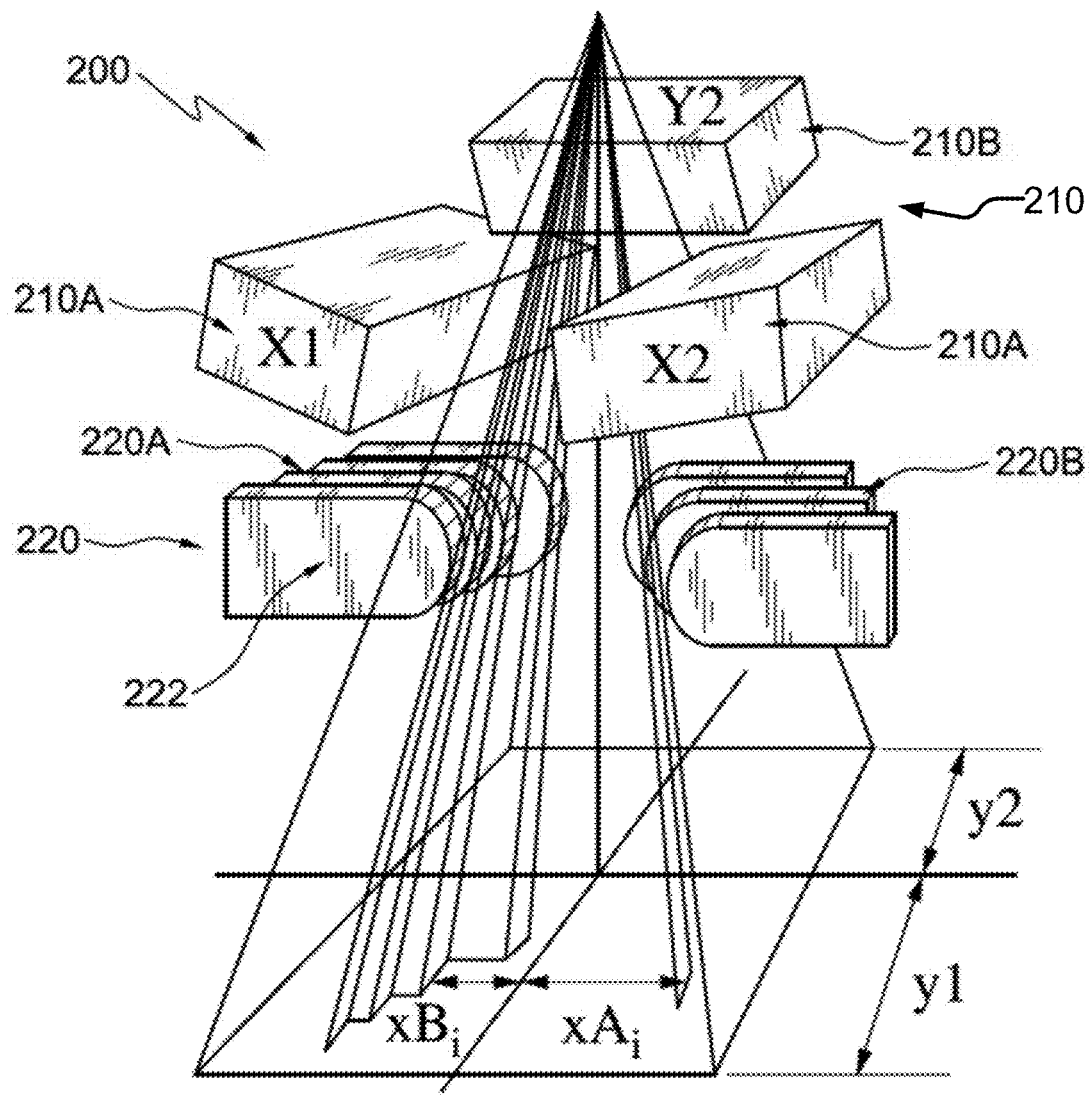
FIG. 2 is a schematic view of an example multileaf collimator.

FIG. 2 shows an example beam shaper 200 that includes a jaw system 210 and a MLC 220. Jaw system 210 comprises two sets of orthogonally positioned jaws 210A and 210B (only one of jaws 210B is shown in FIG. 2). Jaws of sets 210A and 210B may be positioned to shape the radiation beam into a rectangular shape. MLC 220 comprises two banks 220A and 220B of collimator leaves 222. Corresponding ones of leaves 222 from banks 220A and 220B may be advanced toward one another or retracted away from one another. Each of collimator leaves 222 may be independently positioned to shape the aperture through which the radiation beam will pass.

Figure 3A:
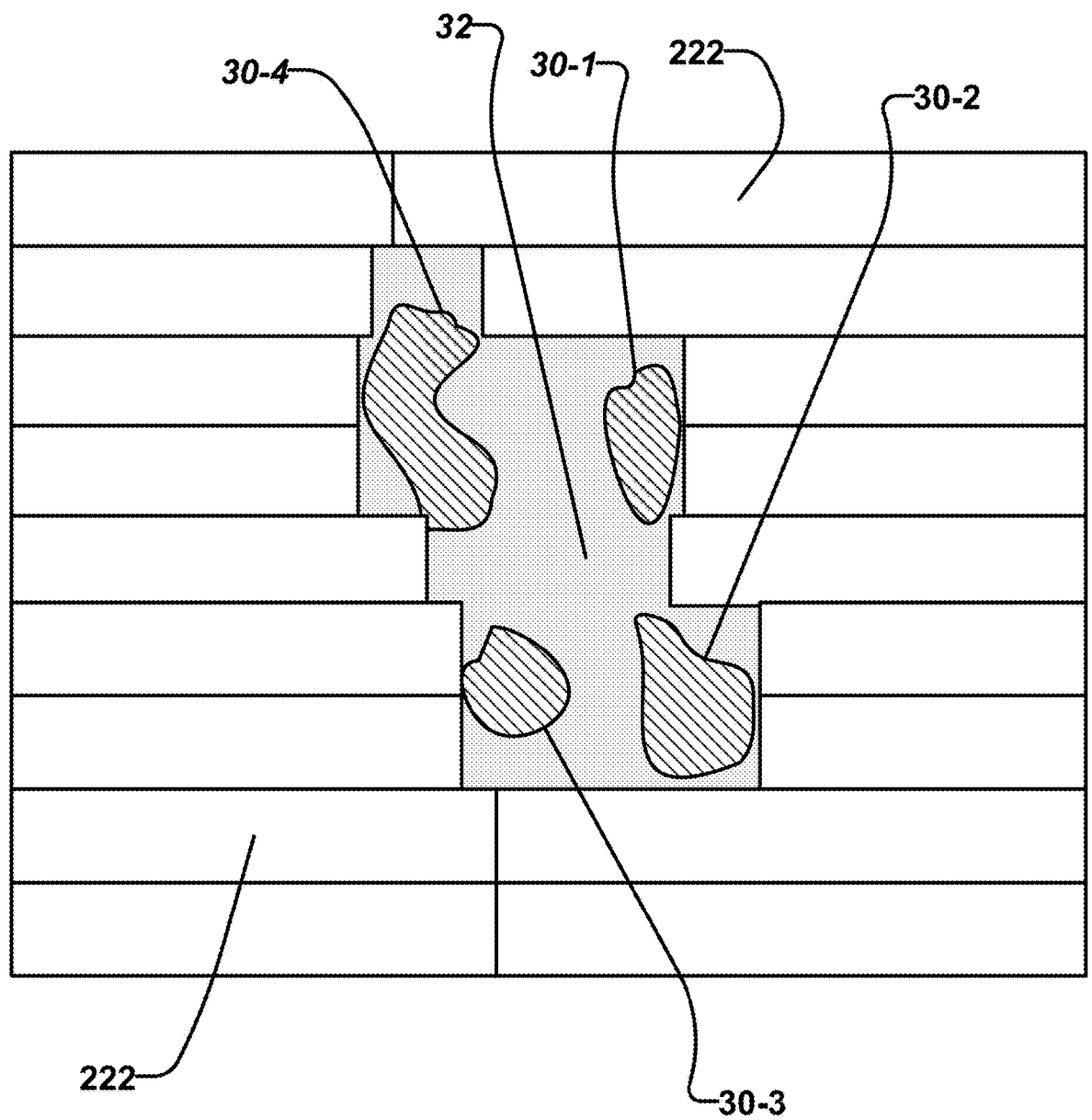
FIGS. 3A and 3B schematically illustrate beam's eye views of a plurality of target volumes.
Figure 3B:
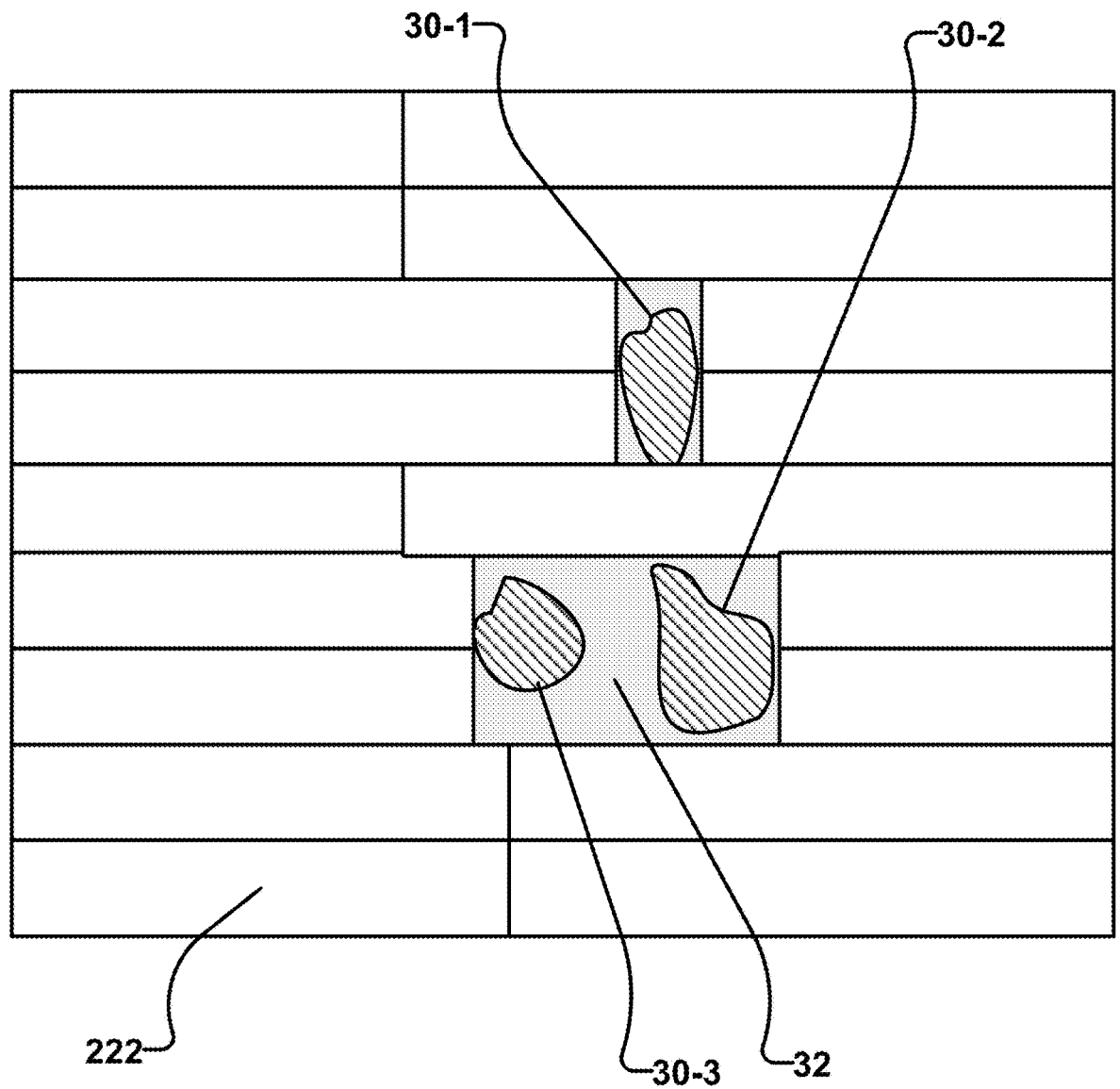

FIG. 3A schematically illustrates a beam's eye view of a plurality of target volumes 30 identified individually as 30-1, 30-2, 30-3, and 30-4. There is no possible configuration of collimator leaves 222 that blocks radiation from reaching the central area 32 surrounded by target volumes 30 and yet does allow radiation to reach all of target volumes 30. FIG. 3B shows that collimator leaves 222 can do a reasonably good job of shaping a radiation beam to expose targets 30 while blocking radiation from reaching central area 32 if target volume 30-4 is deleted. FIGS. 3A and 3B illustrate the general idea that a MLC or other beam shaper can be made to better fit to projections of target volumes from different directions if the set of target volumes is appropriately divided into subsets and collimator configurations are determined separately for each of the subsets.

Figure 4:
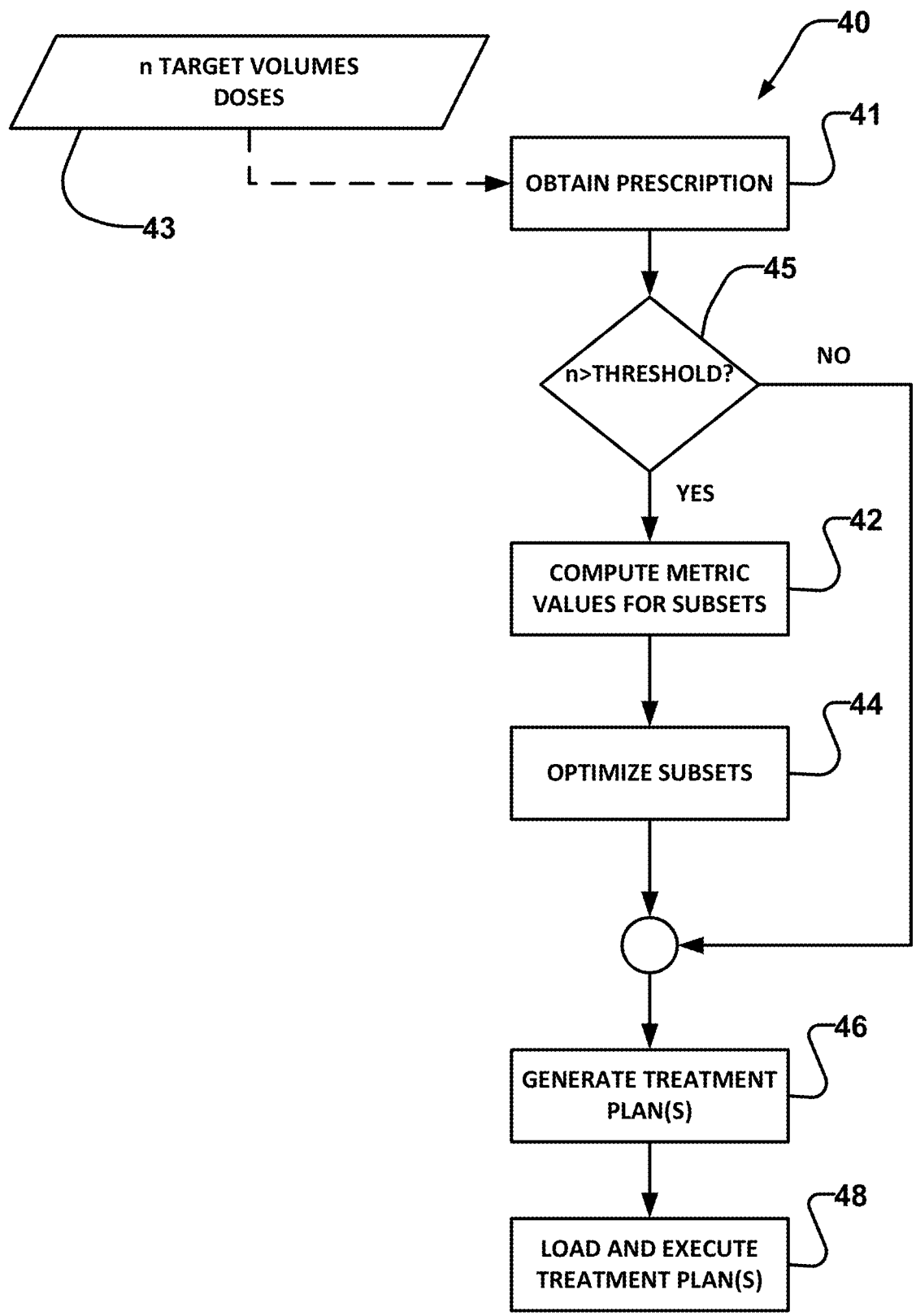
FIG. 4 is a flowchart illustrating a method for implementing a radiation treatment plan according to an example embodiment of the invention.

FIG. 4 is a flowchart illustrating a method 40 according to an example embodiment of the invention. Method 40 may be performed, for example, in a programmed computer system, such as a radiation treatment planning system. Block 41 obtains a prescription which identifies a plurality of target volumes and associates corresponding prescribed doses 43 to each of the target volumes. Prescribed doses 43 may be the same or different for different target volumes. Prescribed doses 43 may be uniform within each target volume or may have a prescribed variation within one or more target volumes.

The target volumes may, for example, be defined by specifying bounding surfaces in a three-dimensional coordinate system and/or by specifying sets of voxels belonging to each of the target volumes. The individual target volumes may be identified by suitable indices, names, pointers or the like. A treatment plan may be developed from pre-treatment imaging such as CT scans in which the locations and extent of areas to be treated can be identified. A three-dimensional target volume may, for example, be determined by adding to an identifiable tumour volume a margin to account for sub-clinical disease spread and an additional margin to account for imprecision in planning and/or delivering the treatment radiation. The target volumes may be defined, for example, using suitable treatment planning software. Some examples of commercially available treatment planning software are: Brainlab iPlan™, Varian Eclipse™, Elekta Monaco™, Elekta Oncentra™, Phillips Pinnacle™, Raysearch RayStation™, Accuray TomoTherapy™, and Elekta Xio™. The target volumes may be represented in a digital data format.

Optional step 45 compares the number of prescribed target volumes to a threshold. If the number of prescribed target volumes equals or exceeds the threshold, then method 40 performs block 42, otherwise performance of block 42 is suppressed. The threshold may, for example, be in the range of 4 to 7.

Block 42 determines values of a metric corresponding to a plurality of subsets of the target volumes. As described below, the metric may be selected to be a metric that correlates to how well a beam shaper will likely be able to conform a radiation beam to the target volumes of a subset. The metric may be chosen such that the value of the metric can be determined with relatively low computational burden. Block 44 identifies an optimal group of subsets of the target volumes based on the values of the metric for the subsets.

Various options exist for constraining what subsets are considered. In a simple embodiment, the system may receive user input that specifies how many subsets may be considered and/or a range of numbers of target volumes that may be included in any subset. In some embodiments, the number of subsets into which the target volumes may be grouped may be determined by calculation based on the total number of target volumes, a degree of clustering of the target volumes, or other factors. For example, the number of subsets may depend on the total number of target volumes according to a set formula. In some embodiments, a system as described herein may perform an optimization to establish an appropriate number of subsets and/or an appropriate number of target volumes to include in each subset. In some embodiments, the number of subsets may be pre-set (e.g. the system may be configured to always use two subsets).

In an example embodiment, a system does not attempt to divide the target volumes into subsets if the number of target volumes is less than a first threshold. If the number of target volumes equals or exceeds the first threshold the system may attempt to find two optimized subsets. Optionally, if the number of target volumes equals or exceeds a second threshold, the system may attempt to divide the target volumes into three optimized subsets.

The number of target volumes to include in each subset may be set or may be calculated. For example, a system as described herein may impose a rule that forces the number of target volumes included in each of a number of subsets to not differ by more than a maximum difference.

There are tradeoffs to be made in deciding how many subsets to use. Where treatment is delivered separately to each subset, increasing the number of subsets tends to increase treatment time. Also, the more separate treatments that are used to deliver the prescribed dose to each target volume, the more leakage radiation the patient may be exposed to. These factors favour using a relatively small number of subsets. On the other hand, by using more subsets the conformation of a MLC or other beam shaper to target volumes may be improved, thereby reducing dose to non-targeted tissues.

Another benefit of the shorter treatment time that can result from grouping more target volumes together at one time (fewer subsets) is reduced motion of the patient during treatment. This can be an important consideration when treating targets in the brain (and elsewhere), especially when OARs are located close to one or more of the target volumes.

Blocks 42 and 44 may be performed in various ways. For example:

Block 42 may identify a plurality of subsets and compute values of the metric for the plurality of subsets and block 44 may subsequently determine the optimal group of subsets.

Block 42 may compute values of the metric for one group of subsets, and block 44 may apply a simulated annealing algorithm (e.g. example method 40A described elsewhere herein) which generates another group of subsets and compares the groups of subsets and selects the more optimal group. This process may be iterated.

Blocks 42 and 44 may apply a brute force approach which: determines values of the metric for every possible subset of the target volumes, identifies every possible group of subsets that are non-overlapping (i.e. such that each target volume is included in only one of the subsets) and include all of the target volumes, and selects the optimal allocation of the target volumes to the subsets based on the values of the metric calculated for the possible subsets.

After the subsets have been identified, a treatment plan may be generated for each of the subsets. Two, three, or more treatment plans may be generated. This is indicated in block 46. The treatment plan may output collimator configurations (e.g. collimator rotation angle and leaf positions) for a plurality of control points. Any of a wide range of radiation treatment planning methods may be applied to determine the collimator configurations. For example, the methods described in PCT patent publication WO 2017/152286, which is hereby incorporated herein by reference for all purposes, may be used to establish the collimator configurations for each subset. As other examples, treatment plans may be generated using commercially available treatment planning software including the examples described elsewhere herein or other suitable treatment planning methods as described in the academic and patent literature.

The treatment plans may be combined, loaded, and executed by a radiation therapy device as indicated in block 48.

With the collimator configurations chosen, one can adjust doses to compensate for the fact that for some angles of radiation incidence, the projections of one or more target volumes of one subset may overlap with the projection of one or more target volumes of another subset. For this reason it is possible that delivering radiation treatment to one subset using the collimator angles developed in block 46 will also incidentally deliver dose to areas within target volumes that have been assigned to other subsets. Even if the target volumes assigned to different subsets do not overlap for any angles of incidence that are used, delivering radiation to one subset will generally result in some radiation dose to target volumes of other subsets because of, for example, scattering of radiation and/or leakage of radiation through the collimator.

The amount of radiation delivered to each target volume in one subset as a result of treatment delivered to target volumes in other subsets may be calculated using a simulation. The simulation may, for example, take into account the known radiation scattering properties of tissue, the known radiation beam parameters (e.g. beam energy and fluence), the known properties of the multileaf collimator or other beam shaping device used to deliver the treatments, the directions from which radiation is delivered, and the collimator angle and configuration for each angle.

An optimization may be performed in order to adjust the amount of radiation delivered at different control points for each subset so that after all subsets have been treated, every target volume will have received the prescribed dose but not significantly more than the prescribed dose.

One way to adjust the doses delivered at individual control points to optimize the matching between the prescribed dose for each target volume and the aggregate dose delivered to each target volume is to apply the methods disclosed in US patent application No. 62/510,689 filed 24 May 2017 for COORDINATED RADIOTHERAPY FOR PLURAL TARGETS which is hereby incorporated herein by reference for all purposes.

In order to validate the present technology, the inventors have created a computer simulation that generates synthetic geometries of multiple cranial tumor volumes in realistic clinical scenarios. This computer simulation yields groups of simulated target volumes that represent tumors having centres of mass (COMs) located at anatomically appropriate relative locations and have tumor volumes within a realistic range. The number of target volumes created is selectable.

A radiation treatment plan was created for each group of simulated target volumes. The radiation treatment planning followed the methodology described in PCT publication No. WO 2017/152286. Radiation treatment planning used 2-dimension projection modelling code to model the radiation beam's-eye-view (BEV) of the resulting simulated target volumes throughout the range of incident angles of delivery (referenced here as control points) in the clinical standard cranial template of radiotherapy arcs.

For each BEV, a whitespace function was calculated, the whitespace function given by:

$$W(\theta_{GA}, \theta_{CG}, \theta_{CL}) = w_1 \cdot A_{jaw} - w_2 \cdot A_{PTV} + w_3 \cdot (A_{PTV} \Omega A_{OAR}) + w_4 \cdot A_{MLC} \qquad (1)$$

Where:
W is whitespace (i.e. area in the BEV that is within an aperture defined by the collimator leaves but does not correspond to the projection of a target volume).
$\theta_{GA}$ is the gantry angle.
$\theta_{CG}$ is the couch angle.
$\theta_{CL}$ is the collimator angle.
$A_{jaw}$ is the total rectangular area encompassed by the jaw system.
$A_{PTV}$ is the area of the projection of the target volume(s) in the BEV.
$A_{PTV} \Omega A_{OAR}$ is the area of OARs overlapping with the target volume.
$A_{MLC}$ is the area collimated by the MLC with a conformal fit to the target. In general, $A_{MLC}$ is a function of $\theta_{CL}$.
$w_{1-4}$ are weighting factors which can adjust the priority or inclusion of any of the terms in the equation. For the validation study $w_3$ was set to zero (OARs were not considered), and $w_1$, $w_2$, and $w_4$ were set to 1.

For each control point the whitespace value W was computed for each possible collimator angle to yield a whitespace map. The whitespace map can be conveniently visualized as a plot with control points along the horizontal (X) axis and collimator angles along the vertical (Y) axis. Each (X,Y) point on the plot is associated with a value for W.

An optimal trajectory across the whitespace map may be determined, for example, by using a bi-direction gradient (BDG) algorithm. Such BDG algorithm may be performed over a range of angular motion of a collimator. Different collimators may permit different ranges of angular motion. In some embodiments, the BDG algorithm is performed over a partial range of angular motion of the collimator. In some embodiments, the BDG algorithm is performed over a full range of angular motion of the collimator. In some embodiments, the BDG algorithm is performed over a collimator angular motion range of −90 to +90 degrees. In some embodiments, the BDG algorithm is performed over a collimator angular motion range of −180 to +180 degrees. An example of a BDG algorithm is as follows:

1. Beginning at the first control point (control point=1) and the first valid collimator angle (e.g. collimator angle=−90 degrees), define a trajectory by moving to the next control point, and choosing the collimator angle which corresponds to the lowest value of Equation 1, within an allowable range of collimator motion (max $d\theta_{CL}/dCPt$) from the current collimator position. When the final control point has been reached, sum the values of whitespace from all ($\theta_{CL}$,CPt) coordinates in the trajectory.

2. Repeat step 1, beginning at other valid collimator angles for control point 1. Step 2 may for example repeat step 1 for collimator angles in an allowable range that are separated by a desired increment angle. This may be done, for example, by incrementing the collimator angle used for control point 1 in the last iteration of step 1 by an increment angle Δ and repeating until an end of the allowable range of collimator angles is reached. Step 1 may initially set the collimator angle for control point 1 to one end of the allowable range. Step 2 yields summed values of whitespace for trajectories starting at reasonably closely spaced collimator angles at control point 1 (e.g. step 2 may determine trajectories for all collimator angles given by $\theta_1 + n\Delta$ subject to $\theta_1 \le \theta_1 + n\Delta \le \theta_2$ where $\theta_1$ and $\theta_2$ are ends of an allowable range of collimator angles and Δ is an angular increment and n is an integer.

3. Repeat steps 1 & 2 with the whitespace map flipped vertically. This creates gradient trajectories built starting from the last control point and working toward the first control point.

4. Find the trajectory defined from steps 1-3 with the minimum accrued total whitespace score.

For every synthetic geometry created, a whitespace map and trajectory were designed, and parameters used in the geometry were recorded. These parameters included all whitespace values contained in the whitespace map, the total accumulated score via traversal of the whitespace map using the BDG algorithm, the volumes of the targets, and the COM of every target. These parameters were sorted based on the total number of targets in the synthetic anatomy. Some embodiments of the invention apply some or all of the above-noted steps to generate treatment plans for subsets of sets of target volumes.

The sum of all values stored in the whitespace map plotted against the total accumulated score via traversal of the whitespace map using the BDG algorithm is plotted in FIG. 5 for each number of targets.

FIGS. 5A to 5I show that the achievable quality of an arc therapy treatment plan (as indicated by the amount of radiation delivered to non-target areas) tends to be lower in the case where the plan attempts to treat more than five target volumes at one time. As the number of target volumes is increased to 6 or more, the total integrated whitespace of a map increases significantly (i.e. the data reaches farther to the right on the x-axis). This is because, as the number of targets increases, the likelihood that more than one target will lie in the path of one or more opposed leaf pairs in the MLC also increases—a condition that is sufficient for the creation of whitespace under most circumstances. The data also indicates that as total integrated map whitespace increases, there is, on average, a concomitant increase in the integrated whitespace along the chosen collimator trajectory.

When there are 5 targets or fewer, it is frequently possible to find a collimator trajectory through the map that produces a trajectory whitespace value that is small or even 0. When the number of targets is larger than 5, the validation data (n=500) did not produce a single trajectory whitespace value that was 0. This provides a motivation to divide large groups of targets into subgroups such that the subgroups are better adapted for optimal collimation.

One way to optimally divide a given set of target volumes into subsets is the brute force approach of identifying all possible ways to divide the target volumes into subsets, generate a radiation treatment plan for every one of these ways, and compare the plans to find a best plan using a criterion such as best fit of delivered dose to prescribed dose. Such a brute force approach is undesirably computationally intensive in many cases, especially those cases involving more than a few target volumes.

For example, there are 252 distinct ways to divide a set of 10 target volumes into two subsets where each subset contains 5 target volumes. There are many more possibilities if one allows more than two subsets or if one allows subsets to contain more or fewer target volumes or if the prescription specifies doses for more than 10 target volumes. It is computationally intensive to generate and evaluate even one treatment plan. Evaluating hundreds or thousands of treatment plans to pick the best one for an arbitrary number of targets is currently impractical.

Embodiments of the present invention identify possible ways to divide a set of target volumes into subsets and use a metric to identify an optimized way to assign the target volumes into subsets. The metric may be based on a metric value computed for each subset. The metric values for each subset in a possible grouping of target volumes into subsets may then be combined to provide a basis for selecting an optimized one of the possible groupings of target volumes.

For example, consider the very simple case of four target volumes identified as A, B, C, and D (note that the methods described herein are particularly advantageous in the case of 6 or more target volumes but using only four target volumes makes this example simpler). If we impose the constraint that every subset should include at least two target volumes, then the target volumes may be grouped in three ways as follows:

AB and CD;
AC and BD; and
AD and BC.

In this trivial example, one can compute a metric value for each allowed subset (i.e. AB, AC, AD, BC, BD, and CD). These metric values may then be combined to give an overall metric for each of the groupings. The overall metrics may be used to select an optimized one of the groupings of subsets. The metric may optionally be determined for the full set of target volumes (e.g. ABCD). The overall metrics for the optimized one of the groupings of subsets and the full set of target volumes may be compared.

This example has only three possible groupings of target volumes and so the grouping with the best overall metric can readily be identified by brute force (i.e. determining overall metrics for every possible grouping and selecting the grouping providing the best overall metric). In cases where there are more target volumes and, consequently, many more possible groupings of the target volumes into subsets, one can optionally determine an optimized grouping using a method that does not need to determine the overall metric for each possible grouping into subsets. Some examples of such alternative approaches include:

simulated annealing;
finding the best overall metric in a suitably large random sampling of possible groupings.

As noted above, the metric may be selected to have a value that correlates to expected achievable quality of a therapy treatment plan but to be significantly less computationally intensive than generating a therapy treatment plan.

One input to the metric may, for example, comprise dimensions of a minimum bounding volume that encloses the target volumes in a subset. Such input represents, for example, an overall geometry of the target volumes in the subset. In preferred embodiments, such input comprises dimensions of a minimum bounding volume that encloses centers of mass (COMs) of the target volumes in a subset. Using COMs may increase computational efficiency of determining the metric. The bounding volume may, for example, be a rectangular prism or an ellipsoid. The dimensions may, for example, comprise lengths of three perpendicular axes of the bounding volume.

In some embodiments, the orientation of the bounding volume is fixed. In other embodiments the orientation of one or more axes of the bounding volume is adjustable either or both of by way of user input and in response to analysis of the spatial distribution of the prescribed target volumes. As an example of the latter, the bounding volume may be oriented such that axes defining the bounding volume align with principal axes of the distribution of target volumes to which the bounding volume is being applied. Providing an adjustable orientation for the bounding volume may be advantageous, for example, in cases where a radiation treatment plan may use different arcs (or other radiation source trajectories) for delivering radiation to different subsets of the target volumes.

In preferred embodiments, another input to the metric is the volume of each target volume included in the subset for which the metric is being computed.

In an example embodiment, the metric value for a subset is a function of a representative value of the dimensions of the bounding volume and a representative value of the volumes of each of the target volumes. The representative values may, for example, comprise average, median, or maximum of the dimensions of the bounding volume.

An optimized grouping into subsets of a set of prescribed target volumes may be found by seeking an extremum (e.g. maximum or minimum) of an overall metric which combines the metric values for the subsets in a possible grouping.

The following examples provide metrics which are minimized for an optimized subset. Those of skill in the art will understand that there are equivalent metrics which are maximized for an optimized subset. For example if M is a metric that identifies an optimized subset when minimized, 1/M is an example equivalent metric that would identify the optimized subset when maximized.

An example embodiment applies a metric M which combines (e.g. by multiplication or addition) a representative value for magnitudes of the target volumes of a subset by a representative value for dimensions of a bounding volume for the subset. A compression function is optionally applied to the result of the combination. A specific example of such a metric is given by:

$$M = \log(\overline{V} * \overline{A}) \quad (2)$$

where M is the value of the metric for a subset, $\overline{V}$ is the mean of all target volumes in the subset of target volumes being considered, and $\overline{A}$ is the mean of the magnitude of the three axes in the minimum bounding ellipse for all COMs in the subset. A compression function (in this example a base 10 logarithm) is optional but can be convenient for reducing the range of metric values. A metric value for a metric like that of Equation 2 may be computed for each subset of target volumes being considered.

Another example metric that may be used in place of Equation 2 or combined with Equation 2 involves a linear combination of a term based on volumes of the target volumes in the subset and a term based on a length characteristic of the bounding volume. An example of such a metric is given by:

$$M = \frac{a * \sum V}{\sigma_V} + \frac{b * \sum S}{\sigma_S} \quad (3)$$

where M is the value of the metric, V is the volume of a target volume in the subset of target volumes being considered, a and b are weighting factors, $\sigma_V$ is a normalization factor. The normalization factor may, for example, be set to:
the standard deviation of the volumes V of the target volumes in a population of target volumes;
the standard deviation of volumes V of the subsets of target volumes in a population of target volumes;
the standard deviation of volumes V of the target volumes for which a treatment plan is being developed; or
the standard deviation of volumes V of the target volumes in one or more subsets for which a treatment plan is being developed.

$\Sigma S$ is the sum of the lengths of the axes of the bounding volume (i.e. S is a length of an axis of the bounding volume), and $\sigma_S$ is a normalization factor that may be set, for example, to equal the standard deviation of sums of axes for bounding volumes in populations of subsets of target volumes used in radiation treatments. In an example non-limiting embodiment a=0.6 and b=0.4.

An overall metric for a grouping of subsets may, for example, be determined by a quadrature addition of all metric values for all subsets in the grouping. For example, in the case where a grouping includes three subsets, $M_1$, $M_2$, and $M_3$, example ways to generate an overall metric include:

$$M_{OA} = M_1^2 + M_2^2 + M_3^2 \quad (4)$$

$$M_{OA} = \sqrt{M_1^2 + M_2^2 + M_3^2} \quad (5)$$

where $M_{OA}$ is the value of the overall metric for the grouping of subsets.

In some embodiments, combining metric values for individual subsets is performed by applying a function which includes a term that penalizes large differences between the metric values for the individual subsets. For example, the overall metric may be represented by:

$$M_{OA} = \Sigma_j M_j + \Sigma_{j \neq k}(M_j - M_k) \quad (6)$$

where j and k are indices that range over the number of subsets (e.g. for 3 subsets, j and k may each range over the values 1, 2 and 3). This overall metric aims to minimize the sum of metric values for all subsets of target volumes but penalizes the situation in which a very low metric value for one subset results in high metric values for one or more other subsets.

Another example of an overall metric is given by:

$$M_{OA} = \sqrt{\Sigma_j M_j^2} - \Sigma_{j \neq k}(M_j - M_k) \quad (7)$$

FIGS. 6A to 6I show the data from FIGS. 5A to 5I in which each data point is replaced by a symbol which indicates the value of the metric of Equation 2 corresponding to that data point. FIGS. 6A to 6I show clearly that a low value of the metric is correlated with an increase in ability to generate a collimator trajectory that is associated with a minimal quantity of whitespace. Thus using a metric like that of Equation 2 to select subsets of target volumes can lead to higher quality radiation treatment plans.

FIGS. 6A to 6I show that the metric of Equation 2 correlates with both the trajectory whitespace value and the total map trajectory value. Calculating the value of M using Equation 2 for a subset of target volumes is vastly less computationally intensive than determining an optimized trajectory for the same subset of target volumes. Such a metric may be used to quantify the optimality of a given subset of targets from readily determinable geometric parameters (namely COM and target volume).

Figure 4A:
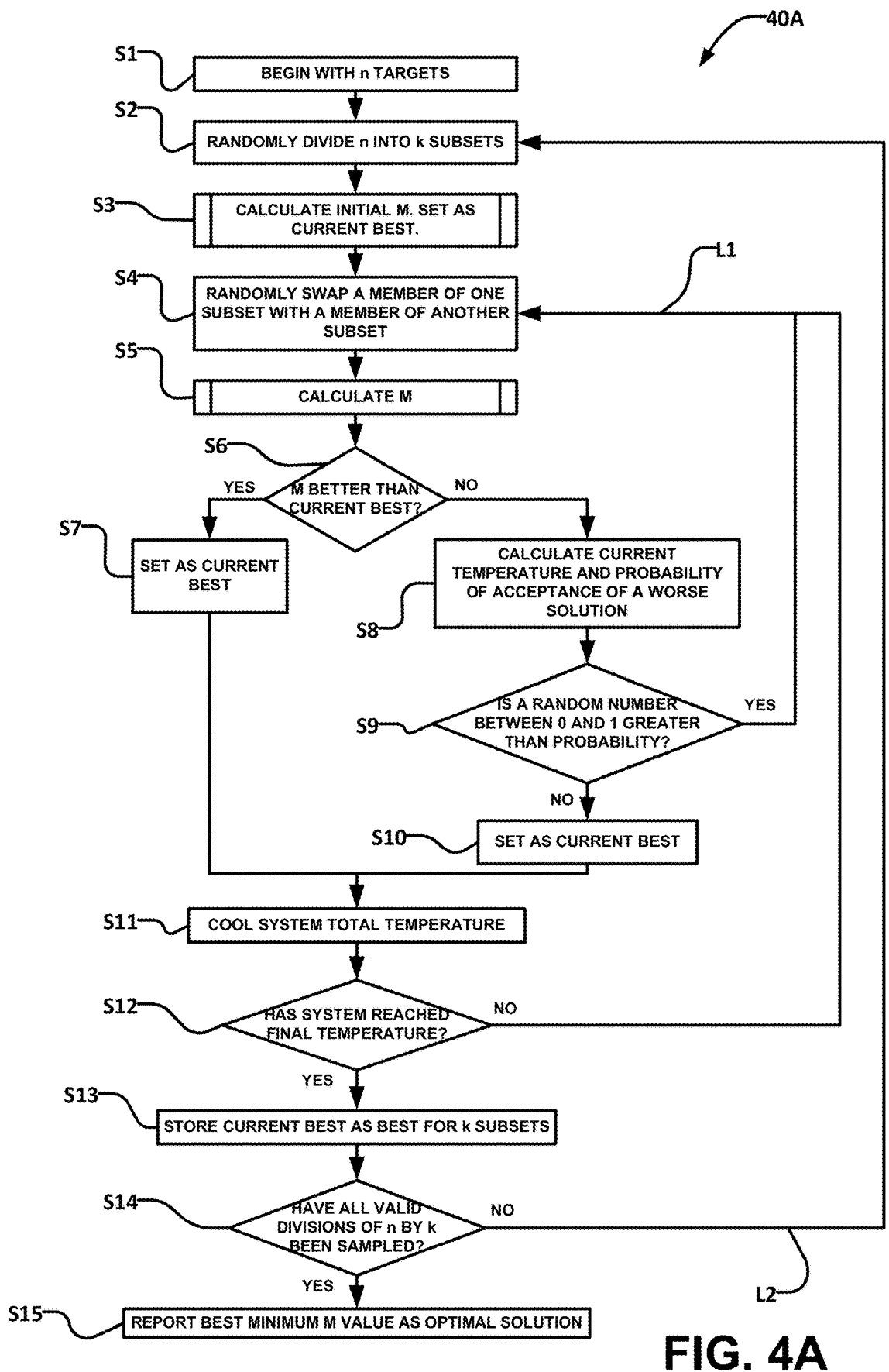
FIG. 4A illustrates an example method which may be applied to determine an optimal way to group target volumes into subsets using a metric.

FIG. 4A illustrates an example method 40A which may be applied to determine an optimal way to group n target volumes into k subsets using a metric M. Instead of testing for all possible groupings of the n target volumes into subsets and computing the overall metric for each grouping, method 40A applies simulated annealing. Method 40A starts by grouping the n target volumes into k subsets and then attempts to improve the overall metric by exchanging target volumes from different subsets one pair at a time.

Example method 40A begins at S1 by accessing information defining n target volumes. At S2 a starting grouping of the target volumes into k subsets is obtained. The starting grouping may be obtained randomly, by assigning target volumes to subsets in an order, or the like. Any grouping of the target volumes into k subsets may be determined at S2. At S3 an overall metric for the starting grouping is computed. The value of this overall metric is saved, associated with the starting grouping, and identified as a current best.

After block S3, method 40A executes loop L1 which repeats in an attempt to find an optimal grouping into k subsets that is better than the starting grouping identified in S2. Loop L1 starts at S4 which changes the allocation of the target volumes into the k subsets. Preferably the change affects relatively few target volumes (e.g. 1 or 2 target volumes). For example, the change may involve moving one target volume from one of the k subsets to another one of the k subsets or swapping a target volume in one of the k subsets with another target volume in another one of the k subsets. This change may be generated randomly or quasi-randomly. S5 determines the overall metric for the new grouping resulting from the change generated by S4. S6 checks to see whether the overall metric for the new grouping is better than the current best. If so, at S7 the new grouping is identified as the current best grouping and the value of the overall metric for the new grouping is saved, associated with the new grouping, and identified as the current best.

Even if S6 determines that the overall metric for the new grouping is not better than the current best (i.e. a NO result at S6), method 40A may identify the new grouping as the current best grouping with a finite probability which depends on a temperature value that ramps down as method 40A continues to repeat loop L1. The temperature value may, for example, be initialized before processing of L1 commences. The temperature value may be reduced based on a number of times that loop L1 is repeated.

At S8 method 40A determines a probability, based on the current temperature value, that the worse overall metric corresponding to the new grouping should be accepted. The probability in S8 may decrease as the temperature value decreases. The probability in S8 may also decrease as the difference between the overall metric for the new grouping and the overall metric for the current best grouping increases.

At S9 method 40A generates a random number and determines whether that random number lies within a range corresponding to the probability determined in S8. For example, if S8 determines a probability of 1/10 then S9 may determine whether a random number in the range of 0 to 1 falls within the range of 0 to 1/10. If so, then at S10 the new grouping is identified as the current best grouping and the value of the overall metric for the new grouping is saved, associated with the new grouping, and identified as the current best. Otherwise, method 40A returns to S4 to commence another cycle of loop L1.

At S11 the temperature value used at S8 is reduced. At S12 method 40A returns to S4 to commence another cycle of loop L1 if the temperature value has not decreased to a final temperature value. Otherwise method 40A proceeds to S13 which identifies the stored current best grouping as the best grouping.

In the example embodiment illustrated in FIG. 4A, step S4 may be constructed in a way that the changes made do not alter the number of target volumes in any subset but only alter which particular ones of the target volumes are present in each subset. For example, the changes may be constrained to include only exchanging two target volumes. Loop L2 is provided to allow considerations of subsets that have different numbers of target volumes. For example, nine target volumes could be divided into two subsets such that the number of target volumes in each of the subsets is represented by any of the following number pairs: (4, 5), (3, 6), (2, 7), or (8, 1). Loop L2 may be repeated once for each number pair that it is desired to consider. In some embodiments the possible groupings may be constrained to require that each subset has at least a given minimum number of member target volumes or that the numbers of target volumes in any two of the k subsets does not differ by more than a given maximum difference, etc. S14 determines whether all desired divisions of target volumes into subsets have been considered. If not, loop L2 repeats. If so, method 40A proceeds to S15 which outputs the current best grouping of target volumes into subsets. A radiation plan may then be determined for each subset.

The radiation treatment plans may, for example, be determined using an inverse planning algorithm. The radiation treatment plans may comprise control inputs for a linear accelerator or other radiation delivery system. The control inputs, when provided to control the radiation delivery system cause the radiation delivery system to deliver radiation shaped for delivery to the included target volumes.

A prototype implementation of computer code which performed a method as illustrated in FIG. 4A was used to find an optimum grouping of the target volumes of a synthetic random geometry with nine target volumes into two subsets, one subset including five target volumes and one subset including 4 target volumes. The prototype software converged on a solution in 11 seconds. This solution is presented in FIGS. 7, 8 and, 9A to 9I.

Figure 7:
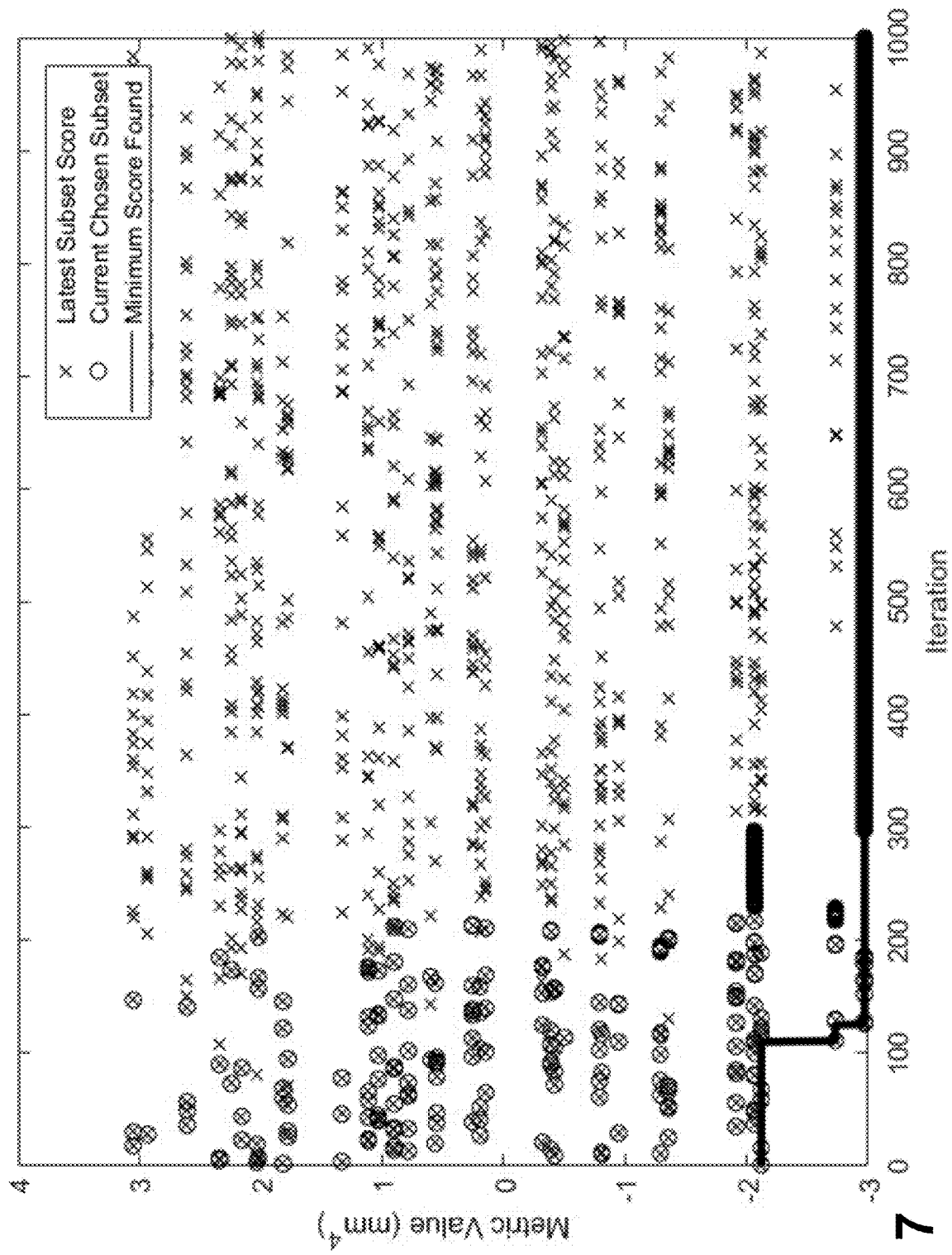
FIG. 7 illustrates the convergence of the method represented in FIG. 4A using simulated annealing.

FIG. 7 illustrates the convergence of the system using simulated annealing. The points marked with an "x" represent the overall metric value at each attempt for grouping. The points marked with an "o" indicate the system's current selection for grouping as it becomes more selective as the simulation proceeds. The black line indicates the minimum value found as a function of iteration.

Figure 8:
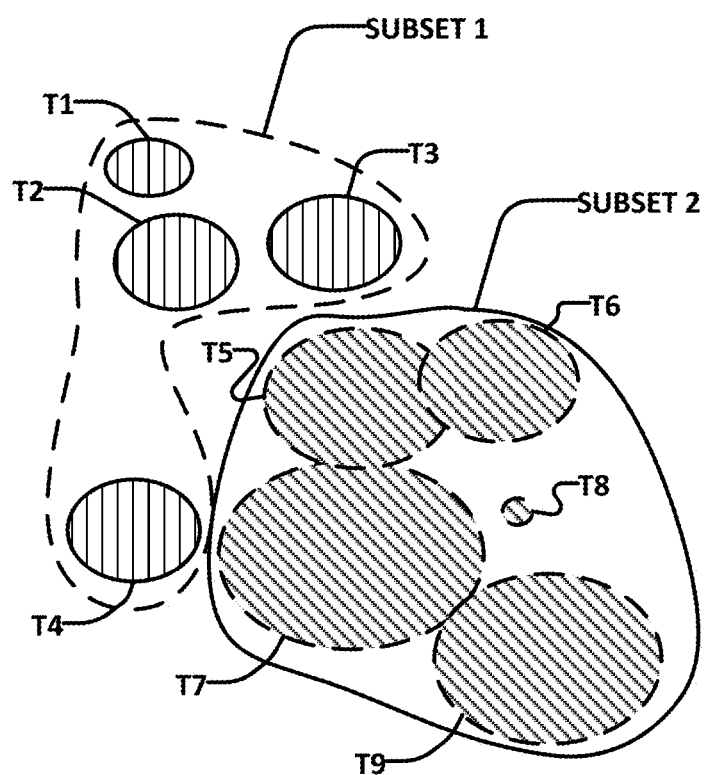
FIG. 8 is a beam's-eye-view from one direction showing the grouping of nine target volumes into two subsets by an example simulated annealing system.

FIG. 8 is a BEV from one direction showing the grouping of the nine target volumes T1 to T9 into two subsets (i.e. subset 1 and subset 2 shown in FIG. 8) by the simulated annealing system.

Figure 9:
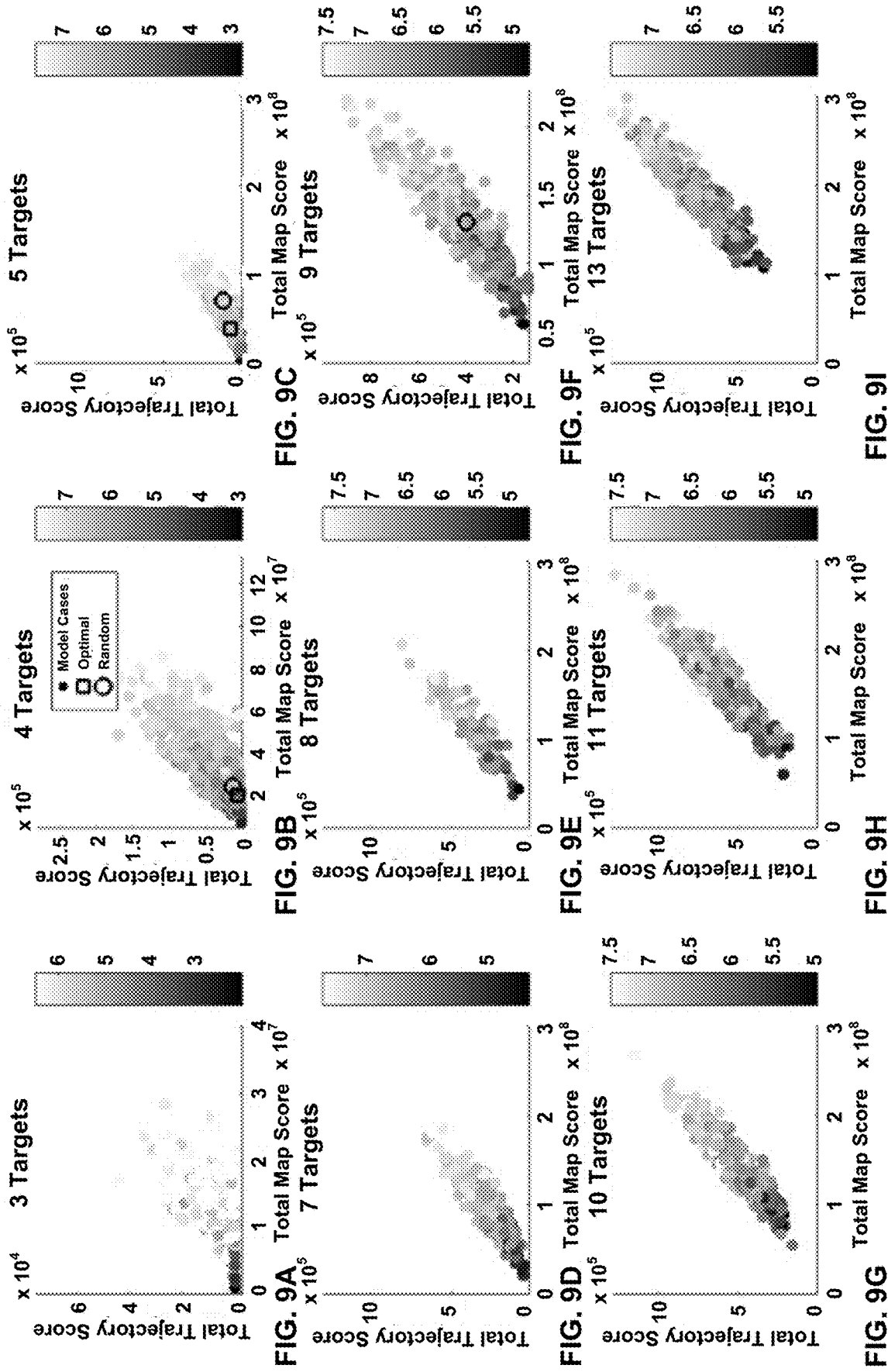
FIGS. 9A to 9I show the same data as shown in FIGS. 6A to 6I with the location of an example optimal solution indicated by a square marker.

FIGS. 9A to 9I show the same data as shown in FIGS. 6A to 6I with the location of the optimal solution indicated by a square marker (e.g. FIGS. 9B, 9C and 9F). A non-optimal nine target volume set was the initial input. This set of target volumes was broken into two optimized subsets. This dramatically reduced the level of total trajectory score (whitespace measure) achievable in the case.

The circular markers indicate the result of a random selection method for creating subsets. In the random selection method, different groupings of target volumes into subsets were selected at random and the group of subsets having the best overall metric was retained.

Table 1 summarizes measures of the quality of radiation plans created for the original set of nine target volumes, the optimal 4-member subset of the target volumes, and the optimal 5-member subset of the target volumes. In each case, a smaller score is better. The sum of the total trajectory scores for the 4 and 5 target subsets is only about 3% of that for the full 9-target set. The sum of the total map scores for the 4 and 5 target subsets is approximately one-half of the total map score for the full 9-target set.

TABLE 1

Tabulated data of the points displayed in FIG. 7 as circular and square markers.

| | Optimized | Random Test | Initial Score |
|---|---|---|---|
| 4 Target Subset | | | |
| Normalized Total Trajectory Score | 0.00004 | 0.00009 | |
| Normalized Total Map Score | 0.15155 | 0.17942 | |
| 5 Target Subset | | | |
| Normalized Total Trajectory Score | 0.00056 | 0.00090 | |
| Normalized Total Map Score | 0.30227 | 0.54478 | |
| 9 Target | | | |
| Normalized Total Trajectory Score | | | 0.00305 |
| Normalized Total Map Score | | | 1 |

Figure 10:
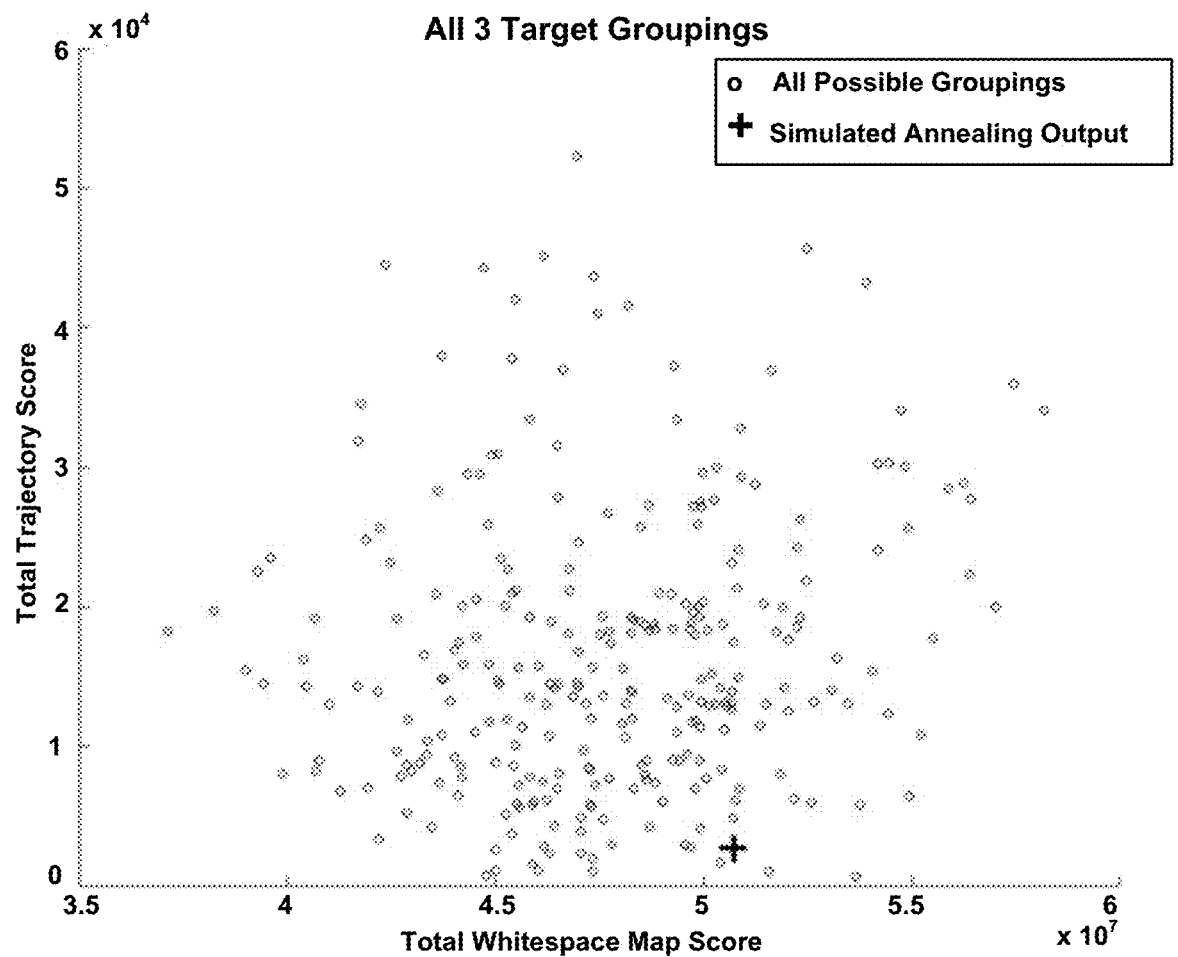
FIG. 10 compares results of the simulated annealing method exemplified by the method shown in FIG. 4A and random generation of solutions.

FIG. 10 compares results of the simulated annealing method exemplified by method 40A and random generation of solutions. FIG. 10 shows trajectory scores for all possible 3-target groupings for one example of a nine-target geometry. The cross indicates the total trajectory score of a grouping determined by simulated annealing (e.g. example method 40A). It can be seen that simulated annealing selected a solution that was much better than most of the possible solutions. Equation 3 was used as a metric for convergence.

Apparatus according to the invention may be configured to perform methods as described herein. The apparatus may, for example, comprise a radiation treatment planning system, an add-on module for a radiation treatment planning system, a radiotherapy system such as a linear accelerator, a control system for a radiotherapy system, and/or the like. Configuration of the apparatus may be provided by configuration information and/or instructions stored in a data store in or accessible to the apparatus and/or hardware design of the apparatus itself.

Figure 11:
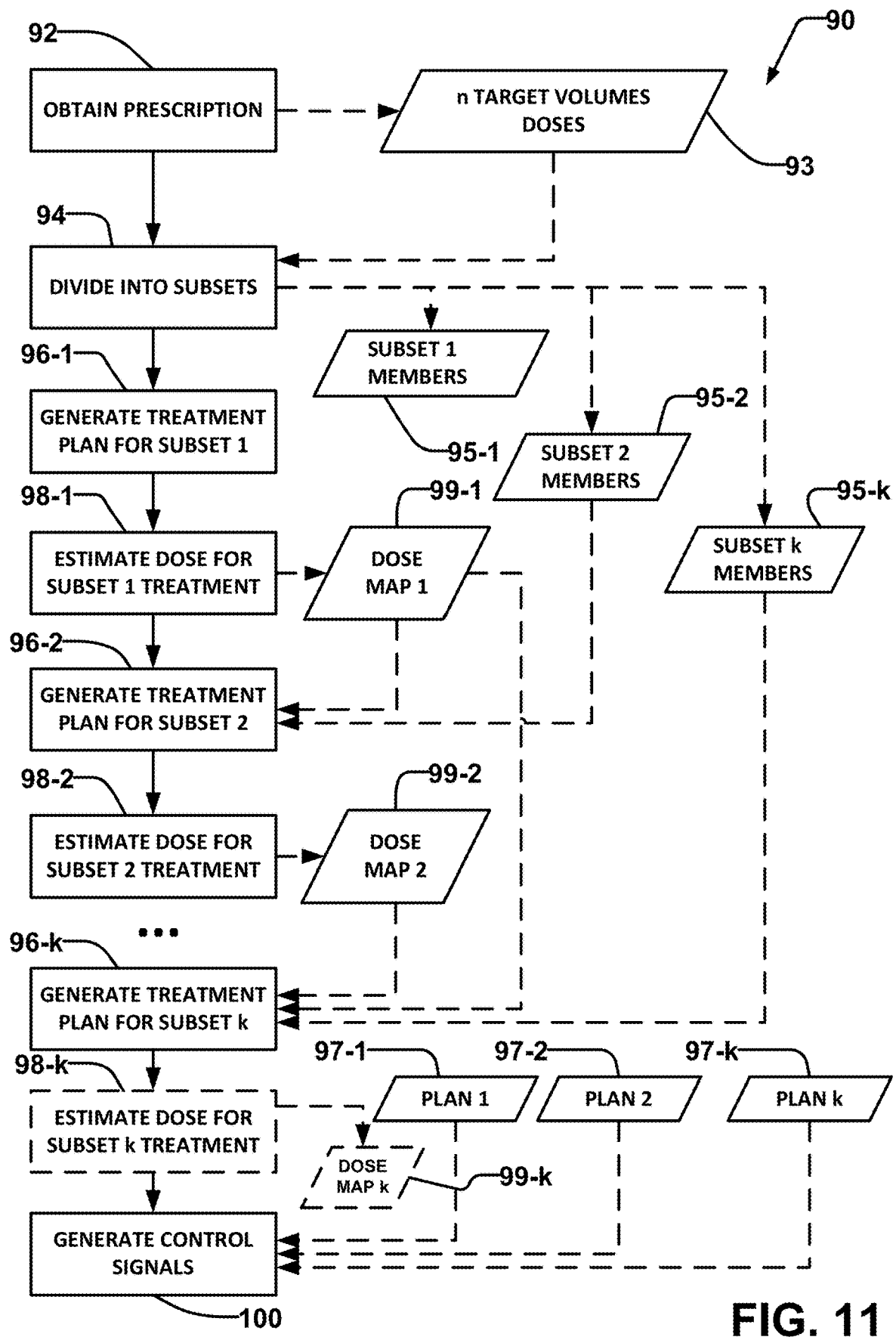
FIG. 11 illustrates a method for developing a radiation treatment plan according to an example embodiment of the invention.

FIG. 11 illustrates a method 90 for developing a radiation treatment plan according to an example embodiment of the invention. Method 90 receives a prescription 93 including a plurality of target volumes at block 92. Block 94 determines an optimized grouping of the target volumes into a plurality of k subsets. k could be, for example, 2, 3, or more subsets. Block 94 may, for example, apply methods discussed above to generate membership data 95-1, 95-2, . . . 95-k for each subset.

Blocks 96-1, 96-2, . . . 96-k generate treatment plans 97-1, 97-2, . . . 97-k for subsets 1, 2, . . . k respectively. Each treatment plan may comprise data specifying collimator rotation angles, collimator leaf positions, and radiation characteristics for each of a plurality of control points. The control points may each correspond to a radiation delivery direction, for example. In a non-limiting example implementation, the control points are spaced apart along an arc at angular intervals of 3 degrees or less.

Blocks 98-1, 98-2 generate estimated dose maps 99-1, 99-2 for the corresponding treatment plan. Block 98-k is optional but advantageously facilitates calculation of a cumulative dose resulting from delivery of the radiation plans for all of the subsets.

In this example, each of blocks 96-2, . . . 96-k receives the dose maps calculated for all of the subsets for which treatment plans have previously been calculated. Block 100 generates control signals for a radiation delivery machine such as a linear accelerator. The control signals may comprise data and/or control instructions that cause the radiation delivery machine to deliver the radiation treatment plans. Block 100 may, for example, generate control signals based on generated treatment plans 97-1, 97-2, . . . 97-k.

In method 90 and variants of method 90, the separate generation of a radiation treatment plan for each subset affords significant flexibility. It is not necessary for different subsets to use the same radiation source trajectories (e.g. arcs) or the same control points or the same radiation beam parameters. In some embodiments, different arcs are specified or determined for delivery of radiation to some or all different subsets of target volumes.

In some embodiments, treatment plans 97-1, 97-2, . . . 97-k are optimized prior to block 100 generating control signals. In some embodiments, treatment plans 97-1, 97-2, . . . 97-k are iteratively optimized. In some such embodiments, some or all of blocks 96-1, 96-2, . . . 96-k are repeated using estimated dose maps 99-1, 99-2, . . . 99-k resulting from corresponding previously established treatment plans for other subsets as base dose levels. For example, block 96-1 may be repeated using the sum of dose maps 99-2 . . . 99-k as a base dose level. This yields a new treatment plan 97-1 and a corresponding new dose map 99-1. If desired this optimization may be continued by supplying the sum of the new dose map 99-1 and previously determined dose maps 99-3 . . . 99-k as a base dose level for repeating block 96-2 to yield a new treatment plan 97-2 having a new corresponding dose map 99-2. Optimizing treatment plans 97-1, 97-2, . . . 97-k, may, for example, minimize exposure of OARs to radiation, reduce treatment time, increase correlation between a prescribed radiation dose and a delivered radiation dose, and/or the like. In some embodiments, the iterative optimization may terminate upon a threshold condition being satisfied. For example, the iterative optimization may terminate upon an estimated total delivered radiation dose deviating from a prescribed radiation dose by an amount within a threshold tolerance.

In an example embodiment, the methods and/or apparatus described in PCT patent publication No. WO 2016/008052, which is hereby incorporated herein by reference for all purposes, are applied to generate trajectories for each subset of target volumes. The trajectories may specify motion of both the patient (e.g. by moving a couch on which the patient is supported) and a gantry supporting a radiation source.

In some embodiments the metric used to optimize grouping of target volumes into subsets and/or the optimization process used to optimize the grouping takes into account geometry of the subsets and alternative radiation source trajectories that could be used to irradiate the subsets.

Figure 12:
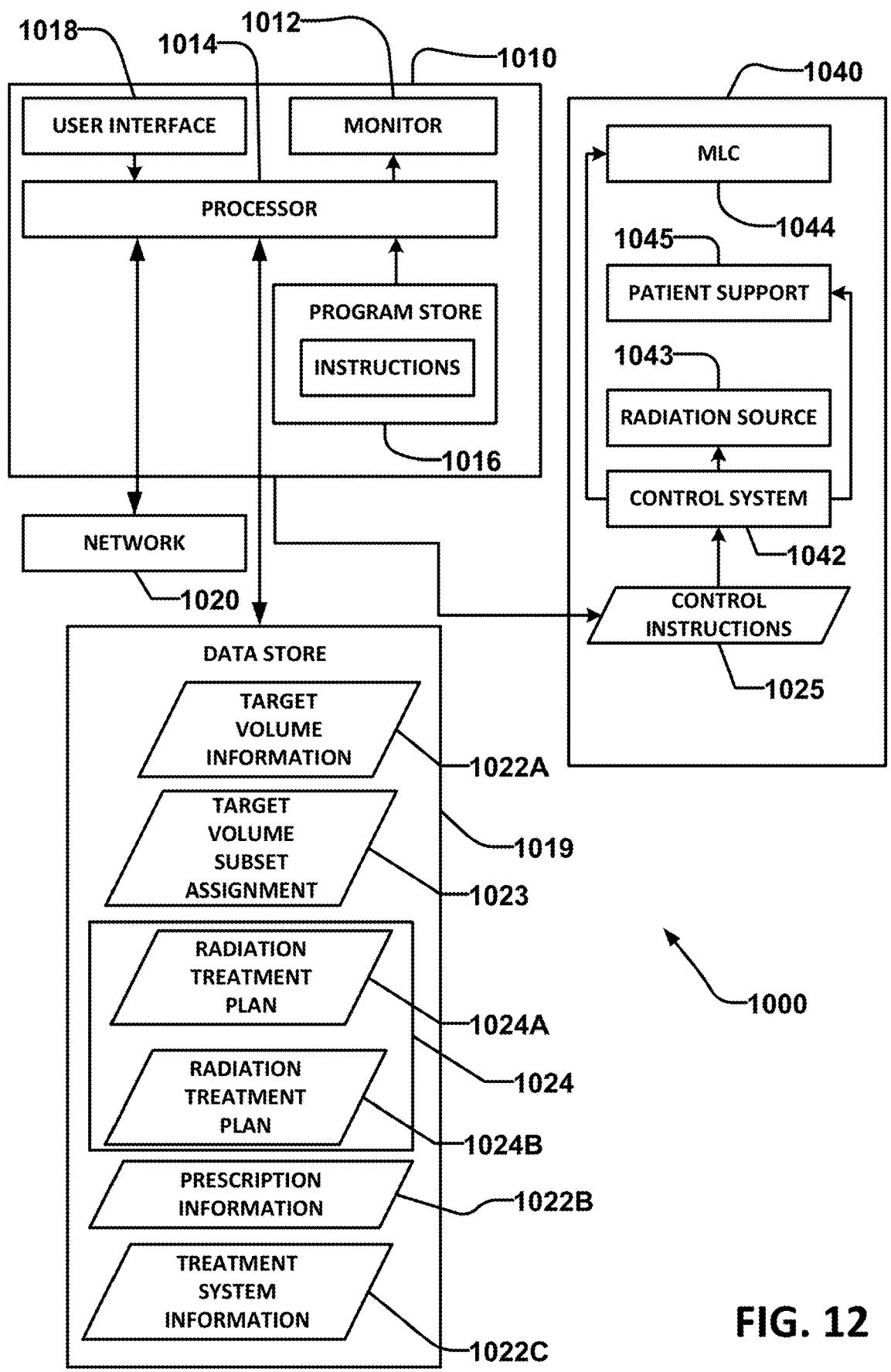
FIG. 12 shows an apparatus for implementing a radiation treatment plan, according to an example embodiment of the invention.

FIG. 12 shows apparatus 1000 according to an example embodiment. Apparatus 1000 includes a radiation treatment planning console 1010, comprising a monitor 1012, data processor 1014, program store 1016 containing instructions, and user interface 1018. Radiation treatment planning console 1010 is connected to access input information for radiation treatment planning, for example, by way of a data communication network 1020, and/or input from user interface 1018, and/or from a local data store 1019, and/or from a connected radiation treatment system 1040. The input information may, for example, comprise:

target volume information 1022A defining the 3D configuration and location relative to a patient of target volumes;

prescription dose information 1022B specifying prescribed doses for the target volumes;

treatment system information 1022C specifying the capabilities and configuration of treatment system 1040. The treatment system information may, for example, specify the configuration of a MLC or other beam shaper of treatment system 1040.

In some embodiments, radiation treatment planning console 1010 is configured to derive one or more of the above types of information from other information (e.g. a set of planning imaging data) with or without guidance from a user.

Radiation treatment planning console 1010 includes software instructions on program store 1016 which cause it to determine optimal subsets of the target volumes for treatment, as described herein.

In some embodiments, local data store 1019 comprises target volume subset assignment data 1023 (e.g. data specifying how target volumes have been assigned into subsets).

Radiation treatment planning console 1010 generates a radiation treatment plan 1024 comprising plural radiation treatment plan components 1024A, 1024 B, . . . 1024 n (only 1024A and 1024B are shown in FIG. 12). Plan 1024 includes a plurality of components with one component 1024A . . . 1024 n for each subset of target volumes. Each component of the radiation treatment plan may specify, for example, a trajectory for use in delivering a radiation treatment to a patient, beam shaper settings for locations along the trajectory, and/or radiation beam settings for locations along the trajectory. Radiation treatment planning console 1010 may additionally generate control instructions 1025, which can be executed by a control system 1042 of radiation treatment system 1040 to implement the radiation treatment plan by delivering radiation to a patient according to plan 1024.

In the illustrated system 1000, radiation treatment system 1040 comprises a radiation source 1043 (e.g. a linear accelerator) equipped with a rotatable multileaf collimator 1044 and a positionable patient support 1045 such as an actuated couch.

The methods and apparatus described herein may be used to treat large numbers of individual targets (e.g. tumors) grouped into two or more subsets. For example, in some embodiments, the methods and apparatus described herein may be used to generate a radiation treatment plan for treating 20 or more tumors or other targets.

Although the systems and methods described herein have been described in association with a whitespace computational model for generating radiation treatment plans, the systems and methods described herein are not limited to only the whitespace computational model but may apply other approaches for generating treatment plans for subsets of target volumes.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

'optimal', 'optimized' and like terms do not require a unique best outcome or result but represent the result of a process directed to achieving an improved outcome or result;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor, cause the data processor to execute a method of the invention. For example, such a program product may contain machine-readable and executable instructions which, when executed by one or more data processors of a radiation treatment planning system cause the radiation treatment planning system to perform a method as described herein. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. By way of non-limiting example only:
 radiation treatment plan components for treating subsets of target volumes identified as described herein may be generated using any suitable radiation treatment planning systems or algorithms that are now or in the future commercially available, described in the patent or technical literature and/or otherwise know to those of skill in the art.

This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for generating a radiation treatment plan for delivery of radiation to a set comprising a plurality of target volumes using a radiation treatment system comprising a beam shaper, each of the target volumes associated with a prescribed radiation dose, the method comprising:
 dividing the set of target volumes into two or more optimized subsets of the set of target volumes by a process comprising:
  computing a metric for each of a plurality of subsets of the set of target volumes, the metric correlated to how well the beam shaper can conform a radiation beam to the target volumes corresponding to each of the plurality of subsets; and
  selecting as the two or more optimized subsets those of the plurality of subsets which contain all of the plurality of target volumes without overlap for which an overall metric obtained by mathematical combination of the metrics for the plurality of subsets is an extremum; and
 determining a treatment plan for each of the two or more optimized subsets, the treatment plans specifying configurations for the beam shaper for control points along a radiation source trajectory, each configuration selected to shape the radiation beam to deliver radiation to the target volumes of the respective subset.

2. The method according to claim 1 comprising providing each of the treatment plans in the form of control signals that may be applied to control the radiation treatment system to deliver radiation using the corresponding trajectory and configurations for the beam shaper.

3. The method according to claim 1 wherein computing the metric for each of the plurality of subsets comprises determining lengths of axes of a three-dimensional bounding volume enclosing centers of mass of the target volumes of the respective subset and computing a function of the lengths of the axes.

4. The method according to claim 3 wherein an orientation of one or more of the axes of the bounding volume is adjustable by at least one of user input and in response to analysis of a spatial distribution of the target volumes and the method comprises setting the orientation of one or more of the axes of the bounding volume in response to analysis of the spatial distribution of the target volumes by orienting one or more of the axes of the bounding volume to align with one or more principal axes of the spatial distribution of the target volumes.

5. The method according to claim 1 wherein determining the treatment plan for each of the two or more optimized subsets comprises selecting different trajectories for delivering radiation to at least two of the optimized subsets.

6. The method according to claim 3 wherein the function combines a representative value for magnitudes of the target volumes of a subset with a representative value for dimensions of a bounding volume for the subset.

7. The method according to claim 1 comprising seeking an optimal grouping of subsets that provides an extremum of the overall metric by applying a simulated annealing algorithm.

8. The method according to claim 7 wherein the simulated annealing algorithm comprises a plurality of iterations, each of the plurality of iterations comprising generating a new group of subsets and determining a value of the overall metric for the new group of subsets.

9. The method according to claim 1 wherein dividing the set of target volumes into the two or more optimized subsets comprises identifying all possible subsets of the set of target volumes and computing the metric for each of the possible subsets.

10. The method according to claim 9 comprising constraining the possible subsets by requiring a number of the target volumes to be included in each of the subsets to be within a set range.

11. The method according to claim 9 comprising constraining the possible subsets by requiring that all of the plurality of target volumes be contained in no more than a set number of non-overlapping subsets wherein the set number is in a range of 2 to 5.

12. The method according to claim 1 wherein determining the radiation treatment plan for one of the optimized subsets comprises taking into account calculated radiation dose that would be delivered to the target volumes of the respective subset by executing a radiation treatment plan for one or more other ones of the optimized subsets.

13. The method according to claim 1 wherein the configurations of the beam shaper comprise rotation angles of the beam shaper along the radiation source trajectory.

14. The method according to claim 1 wherein the metric for each of the plurality of subsets of the set of target volumes is computed according to one of the following equations:

$$M = \log(\bar{V} * \bar{A}); \text{ and}$$

$$M = \frac{a * \sum V}{\sigma_V} + \frac{b * \sum S}{\sigma_S}$$

wherein M is a value of the metric for the respective subset, $\bar{V}$ is a mean of all target volumes in the respective subset, $\bar{A}$ is a mean of lengths of axes of a three-dimensional bounding volume, a and b are weighting factors, $\sigma_V$ is a normalization factor, $\Sigma_S$ is a sum of lengths of axes of a three-dimensional bounding volume and $\sigma_S$ is a normalization factor.

15. The method according to claim 1 wherein the overall metric for the plurality of subsets is computed according to one of the following equations:

$$M_{OA} = M_1^2 + M_2^2 + \ldots + M_k^2;$$

$$M_{OA} = \sqrt{M_1^2 + M_2^2 + \ldots + M_k^2};$$

$$M_{OA} = \Sigma_j M_j + \Sigma_{j \neq k}(M_j - M_k); \text{ and}$$

$$M_{OA} = \sqrt{\Sigma_j M_j^2} - \Sigma_{j \neq k}(M_j - M_k)$$

wherein $K_A$ is a value of the overall metric for the plurality of subsets, $M_1$, $M_2$ and $M_k$ are computed metric values for each respective subset in the plurality of subsets, $M_1$ is a computed metric value for a $j^{th}$ subset in the plurality of subsets and k is a value of a total number of subsets in the plurality of subsets.

16. Apparatus for delivery of radiation to a set comprising a plurality of target volumes, each of the target volumes associated with a prescribed radiation dose, the apparatus comprising:
a radiation treatment system comprising a radiation source and a beam shaper; and
a radiation treatment planning console in data communication with the radiation treatment system, the radiation treatment planning console comprising a processor connected to receive data specifying the set of target volumes to be treated by a radiation treatment plan, the processor configured to:
divide the set of target volumes into two or more optimized subsets of the set of target volumes by a process comprising:
computing a metric for each of a plurality of subsets of the set of target volumes, the metric correlated to how well the beam shaper can conform a radiation beam to the target volumes corresponding to each of the plurality of subsets; and
selecting as the two or more optimized subsets those of the plurality of subsets which contain all of the plurality of target volumes without overlap for which an overall metric obtained by mathematical combination of the metrics for the plurality of subsets is an extremum; and
determine a treatment plan for each of the two or more optimized subsets, the treatment plans specifying configurations for the beam shaper for control points along a radiation source trajectory, each configuration selected to shape the radiation beam to deliver radiation to the target volumes of the respective subset.

17. The apparatus according to claim 16 wherein the processor is configured to provide each of the treatment plans in the form of control signals that may be applied to control the radiation treatment system to deliver radiation using the corresponding trajectory and configurations for the beam shaper.

18. The apparatus according to claim 16 wherein the processor configured to compute the metric for each of the plurality of subsets comprises the processor configured to determine lengths of axes of a three-dimensional bounding volume enclosing centers of mass of the target volumes of the respective subset and computing a function of the lengths of the axes.

19. The apparatus according to claim 18 wherein the processor is configured to adjust an orientation of one or more of the axes of the bounding volume based on at least one of user input and in response to analysis of a spatial distribution of the target volumes and the processor is configured to set the orientation of one or more of the axes of the bounding volume in response to analysis of the spatial distribution of the target volumes by orienting one or more of the axes of the bounding volume to align with one or more principal axes of the spatial distribution of the target volumes.

20. The apparatus according to claim 16 wherein the processor is configured to compute the metric for each of the plurality of subsets of the set of target volumes according to one of the following equations:

$$M = \log(\bar{V} * \bar{A}); \text{ and}$$

$$M = \frac{a * \sum V}{\sigma_V} + \frac{b * \sum S}{\sigma_S};$$

wherein M is a value of the metric for the respective subset, $\bar{V}$ is a mean of all target volumes in the respective subset, $\bar{A}$ is a mean of lengths of axes of a three-dimensional bounding volume, a and b are weighting factors, $\sigma_V$ is a normalization factor, $\Sigma S$ is a sum of lengths of axes of a three-dimensional bounding volume and $\sigma_S$ is a normalization factor.

* * * * *